(12) United States Patent
Ameer et al.

(10) Patent No.: US 9,750,845 B2
(45) Date of Patent: Sep. 5, 2017

(54) BIODEGRADABLE NANOCOMPOSITES WITH ENHANCED MECHANICAL PROPERTIES FOR SOFT TISSUE ENGINEERING

(71) Applicant: Northwestern University, Evanston, IL (US)

(72) Inventors: Guillermo Ameer, Chicago, IL (US); Antonio R. Webb, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 14/083,071

(22) Filed: Nov. 18, 2013

(65) Prior Publication Data

US 2014/0135407 A1    May 15, 2014

Related U.S. Application Data

(63) Continuation of application No. 11/529,064, filed on Sep. 28, 2006, now abandoned.

(60) Provisional application No. 60/721,687, filed on Sep. 28, 2005.

(51) Int. Cl.
| | |
|---|---|
| *A61K 9/14* | (2006.01) |
| *A61L 27/18* | (2006.01) |
| *A61L 27/50* | (2006.01) |
| *A61L 27/58* | (2006.01) |
| *A61K 47/34* | (2017.01) |
| *A61K 47/30* | (2006.01) |
| *A61K 9/00* | (2006.01) |
| *A61K 31/74* | (2006.01) |
| *A61K 31/765* | (2006.01) |

(52) U.S. Cl.
CPC .............. *A61L 27/18* (2013.01); *A61L 27/50* (2013.01); *A61L 27/58* (2013.01); *A61K 9/0024* (2013.01); *A61K 31/74* (2013.01); *A61K 31/765* (2013.01); *A61K 47/30* (2013.01); *A61K 47/34* (2013.01); *A61L 2400/12* (2013.01)

(58) Field of Classification Search
None
See application file for complete search history.

(56) References Cited

U.S. PATENT DOCUMENTS

| | | |
|---|---|---|
| 2,671,444 A | 3/1954 | Pease |
| 4,352,883 A | 10/1982 | Lim |
| 4,409,331 A | 10/1983 | Lim |
| 4,769,038 A | 9/1988 | Bendavid et al. |
| 5,292,328 A | 3/1994 | Hain et al. |
| 5,868,745 A | 2/1999 | Alleyne |
| 5,874,500 A | 2/1999 | Rhee et al. |
| 5,891,076 A | 4/1999 | Fabo et al. |
| 5,993,843 A | 11/1999 | Sakurada et al. |
| 6,051,648 A | 4/2000 | Rhee et al. |
| 6,106,558 A | 8/2000 | Picha |
| 6,146,892 A | 11/2000 | Ma et al. |
| 6,166,130 A | 12/2000 | Rhee et al. |
| 6,221,109 B1 | 4/2001 | Geistlich et al. |
| 6,284,941 B1 | 9/2001 | Cox et al. |
| 6,323,278 B2 | 11/2001 | Rhee et al. |
| 6,423,092 B2 | 7/2002 | Datta et al. |
| 6,461,640 B1 | 10/2002 | Hubbell et al. |
| 6,531,146 B2 | 3/2003 | Calhoun et al. |
| 6,548,728 B1 | 4/2003 | Faries et al. |
| 6,572,878 B1 | 6/2003 | Blaine |
| 6,599,323 B2 | 7/2003 | Melican et al. |
| 6,620,203 B2 | 9/2003 | Atala |
| 6,638,284 B1 | 10/2003 | Rousseau et al. |
| 7,186,789 B2 | 3/2007 | Hossainy et al. |
| 7,195,780 B2 | 3/2007 | Dennis et al. |
| 7,368,124 B2 | 5/2008 | Chun et al. |
| 7,592,017 B2 | 9/2009 | Calhoun et al. |
| 2003/0078588 A1 | 4/2003 | Alleyne |
| 2004/0115771 A1 | 6/2004 | Fertala |
| 2005/0063939 A1 | 3/2005 | Ameer et al. |
| 2005/0208095 A1 | 9/2005 | Hunter et al. |

OTHER PUBLICATIONS

Odian, G., "Principles of Polymeriation," 1993, 3rd Ed. pp. 1-2.
Allemann, "In Vitro Extended-Release Properties of Drug-Loaded Poly(DL-lactic acid) Nanoparticles Produced by a Salting Out Method," Pharmaceutical Research, 10: 1732-1737, (1993).
Andreopoulos, "Properties of Maxillofacial Silicone Elastomers Reinforced with Silica Powder," Journal of Biomaterials Applications, 13: 66-73 (1998).
Arshady, "Preparation of Biodegradable Microspheres and Microcapsules: 2.Polyactides and Related Polyesters," Journal of Controlled Release, 17: 1-21 (1991).
Barichello, "Encapsulation of Hydrophilic and Lipophilic Drugs in PLGA Nanoparticles by the Nanoprecipitation Method," Drug Development and Industrial Pharmacy, 25: 471-476 (1999).
Bilati, "Development of a Nanoprecipitation Mehtod Intended for the Entrapment of Hydrophilic Drugs into Nanoparticles," European Journal of Pharmaceutical Sciences, 24: 67-75 (2005).
Blond, "Enhancement of Modulus, Strength, and Toughness in Poly(methyl (methacrylate)-Based Composites by the Incorporation of Poly(methyl methacrylate)-Functionalized Nanotubes," Advanced Functional Materials, 16: 1608-1614 (2006).
Boehm, "Nanoprecipitation Technique for the Encapsulation of Agrochemical Active Ingredients," J. Microencapsulation, 20: 433-441 (2003).
Bokobza, "Reinforcement of Natural Rubber," Journal of Applied Polymer Science, 85: 2301-2316 (2002).

(Continued)

*Primary Examiner* — James Rogers
(74) *Attorney, Agent, or Firm* — Casimir Jones SC; David W. Staple

(57) ABSTRACT

The present invention is directed to a novel poly(diol citrates)-based nanocomposite materials created using completely biodegradable and biocompatible polymers that may be used in tissue engineering. More specifically, the specification describes methods and compositions for making and using nanocomposites comprised of citric acid copolymers and polymers including but not limited to poly(L-lactic acid) (PLLA) and poly(lactic-co-glycolic acid) (PLGA).

16 Claims, 11 Drawing Sheets

(56) References Cited

OTHER PUBLICATIONS

Bokobza, "Silica and Carbon Black Reinforcement of Natural Rubber," Macromolecular Symposia, 194: 125-133 (2003).
Cadee, "A Comparative Biocompatibility Study of Microsphere Based on Crosslinked Dextran of Ply(lactic-co-glycolic) Acid After Subcutaneious Injection in Rats," Journal of Biomedical Materials Research, 56: 600-609 (2001).
Cascone, "Collagen and Hyaluronic Acid Based Polymeric Blends as Drug Delivery Systems for the Release of Physiological Concentration of Growth Hormone," Journal of Materials Science: Materials in Medicine, 5: 770-774 (1994).
Chorney, "Lipophilic Drug Loaded Nanospheres Prepared by Nanoprecipitation: Effect of Formulation Variables on Size, Drug Recovery, and Release Kinetics," Journal of Controlled Release, 83, 389-400 (2002).
David, "Spring-Mediated Cranial Reshaping for Craniosynostosis," Journal of Craniofacial Surgery, 15: 810-816 (2004).
Dunn, "Synthesis of N-(aminoalkyl) Chitosan for Microcapsules," Journal of Applied Polymer Science, 50: 353-365 (1993).
Finegan, "Surface Treatments for Improving the Mechanical Properties of Carbon Nanofiber/Thermoplastic Composites," Journal of Materials Science, 38: 3485-3490 (2003).
Griffith, "Polymeric Biomaterials," Acta Mater, 48: 263-277 (2000).
He, "Fabrication and Endothelialization of Collagen-Blended Biodegradable Polymer Nanofibers: Potential Vascular Graft for Blood Vessel Tissue Engineering,:" Tissue Engineering, 11: 1574-1588 (2005).
Holland, "Polymers for Biodegradable Medical Devices. 1. The Potential of Polyesters as Controlled Macromolecular Release Systems," Journal of Controlled Release, 4: 155-180 (1986).
Jurvelin, "Mechanical Anisotropy of the Human Knee Articular Cartilage in Compression," Proceedings of the I Mech E Part H Journal of Engineering in Medicine, 217: 215-219 (2003).
Kim, "Stimulation of Osteoblast Responses to Biomimetic Nanocomposites of Gelatin-Hydroxyapatite for Tissue Engineering Scaffolds," Biomaterials, 26: 5221-5230 (2005).
Korhonen, "Comparison of the Equilibrium Response of Articular Cartilage in Unconfined Compression, Confined Compression and Indentation," Journal of Biomechanics, 35: 903-909, (2002).
Lavik, "Tissue Engineering: Current State and Perspectives," Appl. Microbiol. Biotechnol., 65: 1-8 (2004).
Liao, "Hierarchically Biomimetic Bone Scaffold Material: Nano-HA/Collagen/PLA Composite," Journal of Biomedical Materials Research, 69: 158-165 (2004).
Ma, "Synthetic Nano-Scale Fibrous Extracellular Matrix," Journal of Biomedical Materials Research, 46: 60-72 (1999).
MacDonald, "Collagen-Carbon Nanotube Composite Materials as Scaffolds in Tissue Engineering," Journal of Biomedical Materials Research, 74: 489-496 (2005).

Matsumoto, "The Fate of the Inverted Segment of Small Bowel Used for the Replacement of Major Veins," Surgery, 60: 739-743 (1966).
Miyazaki, "Drug Release from Oral Mucosal Adhesive Tablets of Chitosan and Sodium Alginate," International Journal of Pharmaceutics, 118: 257-263 (1995).
Murakami, "Further Application of a Modified Spontaneous Emulsification Solvent Diffusion Method to Various Types of PLGA and PLA Polymers for Preparation of Nanoparticles," Power Technology, 107: 137-143 (2000).
Murakami, "Prepartion of Poly(DL-lactide-co-glycolide) Nanoparticles by Modified Spontaneous Emulsification Solvent Diffusion Method," International Journal of Pharmaceutics, 187: 143-152 (1999).
Okada, "Chemical Syntheses of Biodegradable Polymers," Prog. Polym. Sci., 27: 87-133 (2002).
Parkinson, "The Reinforcement of Rubber by Carbon Black," British Journal of Applied Physics, 2: 273-280 (1951).
Pitt, "The Controlled Parenteral Delivery of Polypeptides and Proteins," International Journal of Pharmaceutics, 59: 173-196 (1990).
Ramay, "Biphasic Calcium Phosphate Nanocomposite Porous Scaffold for Load-Bearing Bone Tissue Engineering," Biomaterials, 25: 5171-5180 (2004).
Ratner, "Biomaterials: Where We Have Been and Where We Are Going," Annu. Rev. Biomed. Eng., 6: 41-75 (2004).
Shiraishi, "Controlled-Release Preparation of Indomethacin Using Calcium Alginate Gel," Biol. Pharm. Bull., 16: 1164-1168 (1993).
Thacharodi, "Collagen-Chitosan Composite Membranes for Controlled Release of Propranolol Hydrochloride," International Journal of Pharmaceutics, 120: 115-118 (1995).
Webb, "Biodegradable Polyester Elastomers in Tissue Engineering," Expert. Opin. Bio. Ther., 4: 801-812 (2004).
Wu, "Preliminary Report on Microencapsulated Islet Transplantation in Experimental Diabetes Mellitus in China," Int. J. Pancreotology, 3: 91-100 (1988).
Xu, "Mechanical Property characterization of a Polymeric Nanocomposite Reinforced by Graphitic Nanofibers with Reactive Linkers," Journal of Composite Materials, 38: 1563-1582 (2004).
Yang, "Fabrication and Surface Modification of Macroporous Poly(L-lactic acid) and Poly(L-lactic-co-glycolic acid) (70/30) Cell Scaffolds for Human Skin Fibroblast Cell Culture," Journal of Biomedical Materials Research, 62: 438-446 (2002).
Yang, "Novel Citric Acid-Based Biodegradable Elastomers for Tissue Engineering," Advanced Materials, 16: 511-516 (2004).
Yang, "Synthesis and Evaluation of Poly(diol citrate) Biodegradable Elastomers," Biomaterials, 27: 1889-1898 (2006).
Zhang, "Synthetic Nano-Fibrillar Extracellular Matrices with Predesigned Macroporous Architectures," Journal of Biomedical Materials Research, 52: 430-438 (2000).
Zhang, "Synthesis and Biocompatibility of Porous Nano-Hydroxyapatite/Collagen/Alginate Composite," Journal of Materials Science, 14: 641-645 (2003).

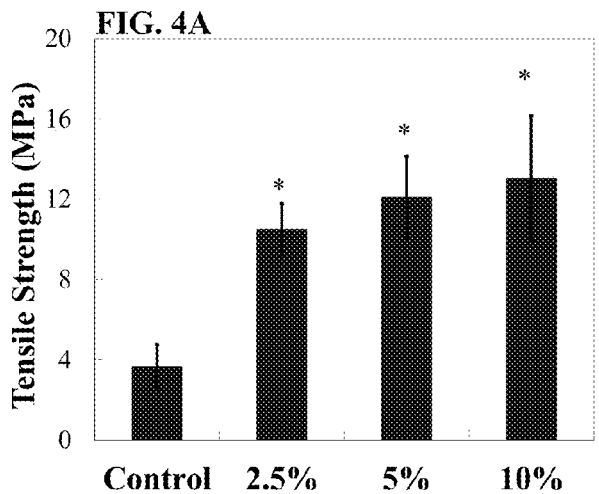
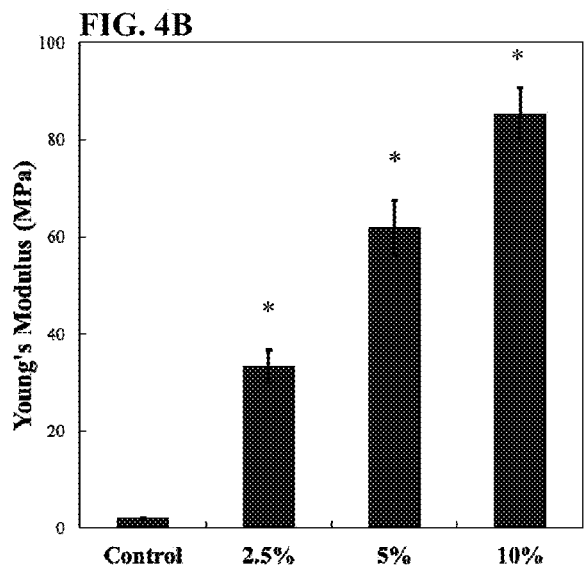
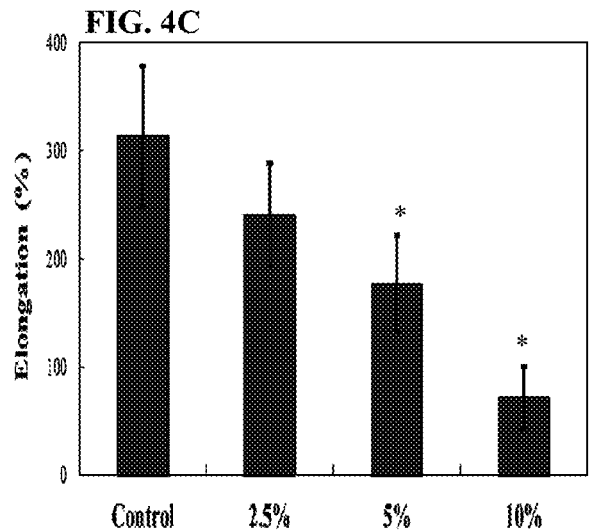

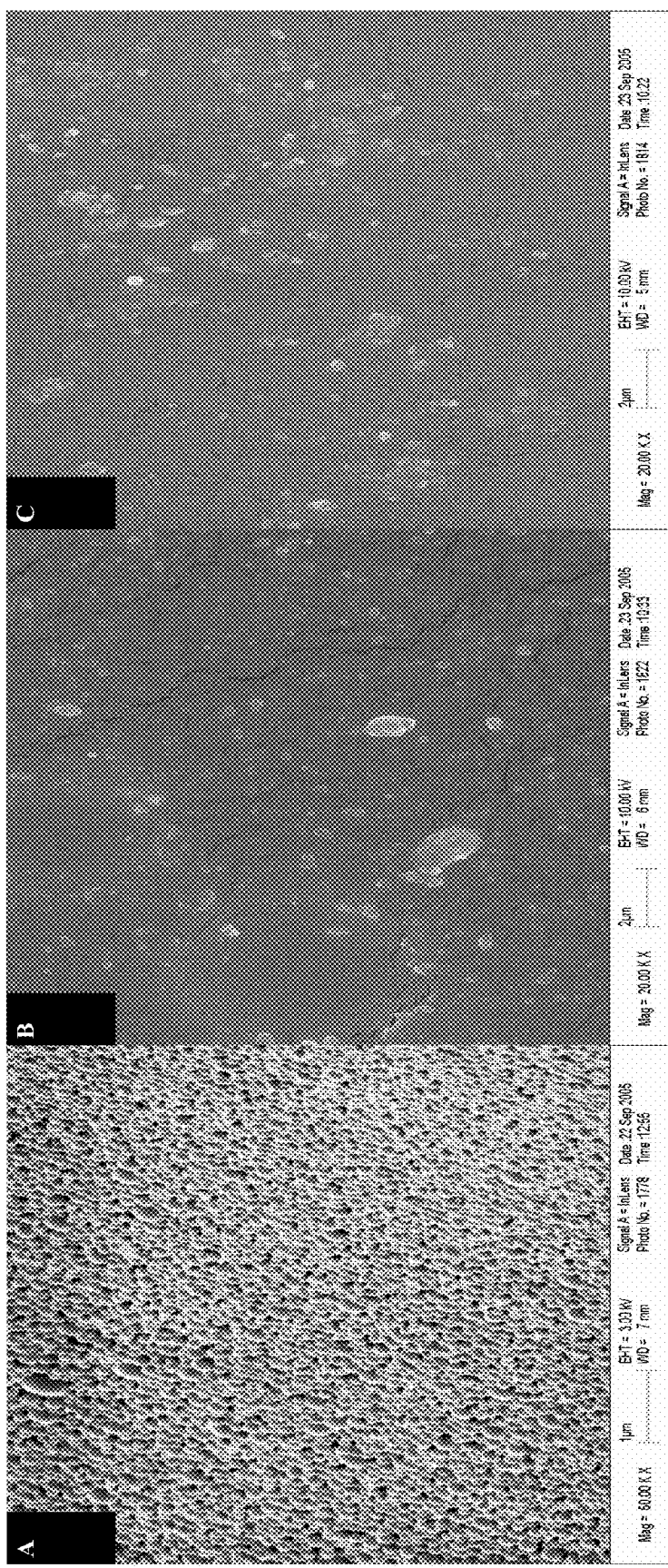
FIGURE 5A-C

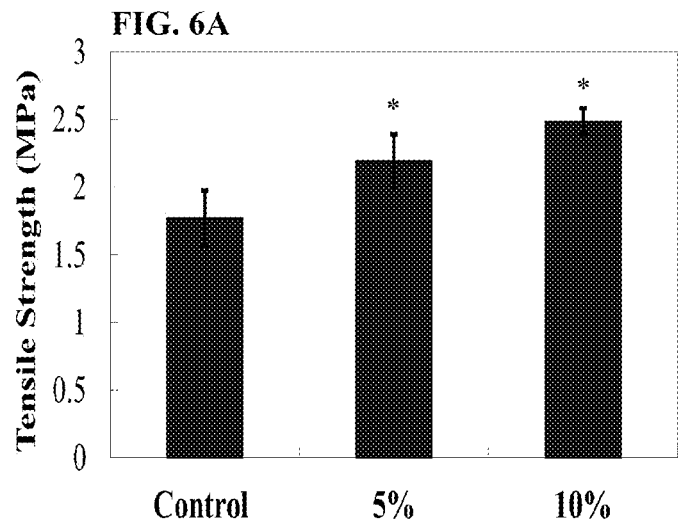
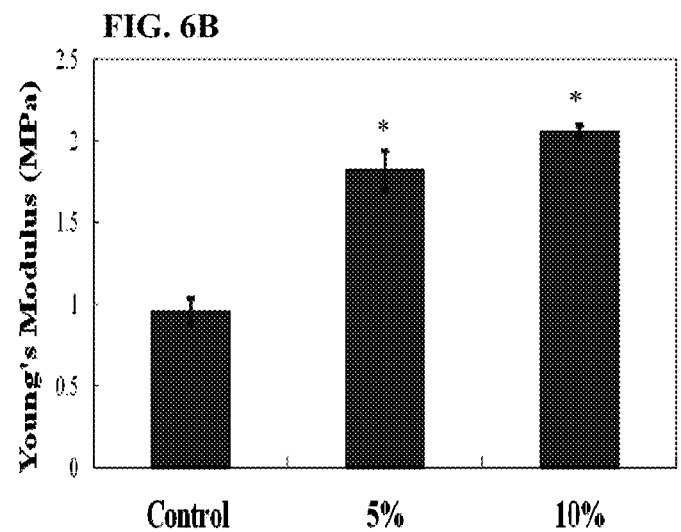
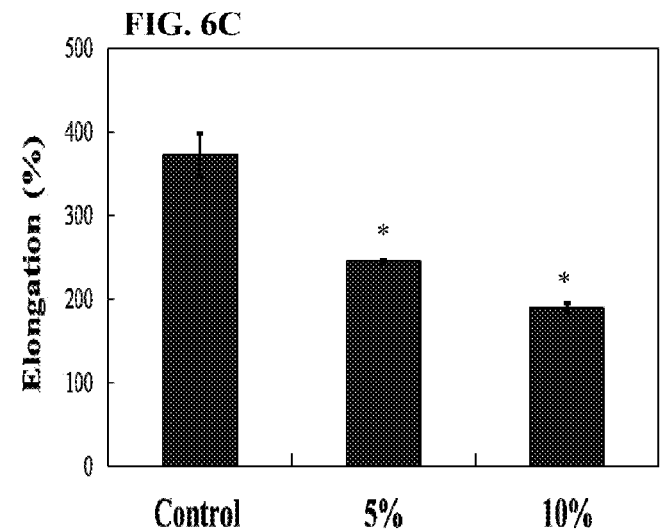

BIODEGRADABLE NANOCOMPOSITES WITH ENHANCED MECHANICAL PROPERTIES FOR SOFT TISSUE ENGINEERING

The present application is a continuation of U.S. patent application Ser. No. 11/529,064, filed Sep. 28, 2006, which claims the benefit of priority of U.S. Provisional Application No. 60/721,687 which was filed Sep. 28, 2005, each of which are incorporated by reference in their entireties.

FIELD OF THE INVENTION

The present invention is generally directed to a substrate used for tissue engineering. The substrate is a biodegradable elastomeric polymer. Methods and compositions for testing and using the same are disclosed.

BACKGROUND

The need for biodegradable polymers in emerging technologies such as tissue engineering, drug delivery, and gene therapy has been fueling a quest for novel biodegradable polymers [13-16]. In particular, biodegradable polymers with elastomeric properties have recently received attention for their potential use in the engineering of soft tissues such as blood vessel, heart valves, cartilage, tendon, and bladder, which exhibit elastic properties. Due to their long history of use in clinical applications, poly(hydroxyortho esters) such as polyglycolic acid (PGA), poly lactic acid (PLA) and copolymers thereof are often used to fabricate three-dimensional porous scaffolds to support cell attachment, proliferation, migration, and extracellular matrix synthesis. The development of a novel family of biodegradable elastomeric polymers referred to as poly(diol citrates) has been reported [1].

Tissues such as blood vessels, cartilage, ligament, and tendon have specific biomechanical requirements for successful functional tissue engineering. These tissues are often subjected to relatively large tensile or compressive forces, so it is important that synthetic scaffolds or implants intended to model such tissues have the necessary tensile strength, elasticity, and compressive modulus to withstand such forces. Ideally, the mechanical properties of the scaffold or implant would approximate those of the natural tissue it is designed to mimic. The reported tensile strength of human cartilage and ligament are 3.7-10.5 MPa and 24-112 MPa, respectively. The reported Young's modulus of cartilage and ligament are 0.7-15.3 MPa and 65-541 MPa, respectively. The reported tensile strength of human coronary arteries is 1.4-11.14 MPa.

It is well known in the art that the mechanical properties of elastomers can be enhanced by the fabrication of composites in which a second component or phase is added to the elastomeric phase. One method by which elastomers can be strengthened and stiffened is by incorporating nanoparticles into the elastomeric matrix [Lavik, E. and R. Langer, Tissue engineering: current state and perspectives. Appl Microbiol Biotechnol, 2004. 65: p. 1-8; Okada, M., Chemical syntheses of biodegradable polymers. Prog Polym Sci, 2002. 27: p. 87-133; Griffith., Polymeric Biomaterials. *Acta Mater,* 2000. 48: p. 263-277; MacDonald, J. *Biomed. Mater. Res. A,* 2005, 74, 489-496]. This is the case in the rubber industry where carbon black nanoparticles can be added to greatly increase the mechanical properties [Lavik, E. and R. Langer, Tissue engineering: current state and perspectives. Appl Microbiol Biotechnol, 2004. 65: p. 1-8]. The nanoparticles act as additional crosslink points to reinforce the network chains and in general, the increase in mechanical properties is inversely proportional to the nanoparticle diameter [Lavik, E. and R. Langer, Tissue engineering: current state and perspectives. Appl Microbiol Biotechnol, 2004. 65: p. 1-8]. Although this method has been used for industrial applications, there have been no reports involving the use of biocompatible, biodegradable nanoparticles to strengthen matrices intended for in vivo use.

Poly(hydroxyortho esters) or other polymers have been mixed with ceramics, glass microparticles, glass nanoparticles, glass nanofibers, or carbon nanotubes to strengthen scaffolds for bone tissue engineering applications and, to a lesser extent, for soft tissue regeneration. However, most of these approaches introduce inorganic and non-biodegradable components into the polymer composite. A non-degradable second phase may interfere with the body's natural remodeling mechanisms as the continuous presence of a foreign material may induce long-term inflammatory responses. Furthermore, the resulting composite does not exhibit the elasticity and flexibility that is important for soft tissue engineering.

Chun et al (U.S. patent application Ser. No. 10/383,369) and Melican et al (U.S. patent application Ser. No. 09/747,489) disclose tissue implants comprising a biodegradable mesh reinforcement component and a biodegradable elastomeric foam component. Ma et al (U.S. Pat. No. 6,146,892) disclose three-dimensional biodegradable matrices comprised of nanofibers. However, Chun et al, Melican et al, and Ma et al do not disclose composites having mechanical properties approaching those of natural soft tissue.

Analogous to rubber which is a three dimensional network of crosslinked polymer chains, poly(diol citrates) are composed of three-dimensional polyester networks formed by reacting citric acid with various aliphatic diols. The mechanical properties could be varied depending on the selection of diols and the applied post-polymerization conditions. In general, longer chain diols have a lower tensile strength and modulus, while increasing polymerization time and/or temperature increase the tensile strength and modulus. Preliminary in vitro cell culture evaluation of poly(diol citrates) showed their great potential as "cell-friendly" materials, as both smooth muscle and endothelial cells attach and proliferate on the surface. Methods of preparation of poly(diol) citrates are described in detail in U.S. patent application Ser. No. 10/945,354 (incorporated herein by reference and also shown in the Examples below). In vivo biocompatibility results show a thin vascularized collagenous capsule after 4 months of implantation with no inflammation. The thickness of this capsule was smaller than that reported for poly(L-lactide-co-glycolide) (PLGA) [17]. A thin vascularized capsule is considered to be beneficial for mass transfer between a cell-based implant and surrounding tissues.

Although the mechanical properties of synthetic polymers, in particular poly(diol citrates), can be varied to meet specific applications, it can be desirable to further increase the strength and stiffness while maintaining the ability to be elongated to many times their original length before rupture. The present invention is directed to optimizing the strength and elasticity of biocompatible scaffolds by preparing a composite comprising an elastomeric polymer strengthened by the presence of a biodegradable polymeric nanostructure.

SUMMARY OF THE INVENTION

The present invention describes a composition comprising a biodegradable elastomeric polymeric component and a biodegradable polymeric nano-structure. The present invention describes a composition comprising a composite of a citric acid polyester having the generic formula (A-B-C)n, wherein A is a linear aliphatic dihydroxy monomer; B is citric acid, C is a linear aliphatic dihydroxy monomer, and n is an integer greater than 1; and a biodegradable polymer used for implantable tissue devices. Preferably, the biodegradable polymer is fabricated into a nanostructure such as a nanofiber, a nanoparticle, or the like.

In specific embodiments, A is a linear diol comprising between about 2 and about 20 carbons. In other embodiments, C is independently a linear diol comprising between about 2 and about 20 carbons. While in certain embodiments, both A and C may be the same linear diol, other embodiments contemplate that A and C are different linear diols. A particularly preferred linear diol is 1,8, octanediol. In other embodiments, one or both of A and C may be 1,10-decanediol. The diol also may be an unsaturated diol, e.g., tetradeca-2,12-diene-1,14-diol, or other diols including macromonomer diols such as polyethylene oxide, and N-methyldiethanoamine (MDEA). This family of elastomers is named as poly(diol citrate). In particularly preferred embodiments, the composition of the invention is dihydroxy poly 1,8-octanediol co-citric acid. Poly(diol citrate) can also form hybrids with other materials like hydroxyapatite to form elastomeric composites.

In some embodiments the nano-structure of the invention is fabricated from a polymer. Preferably the polymer is a biodegradable polymer selected from the group consisting of poly(hydroxyvalerate), poly(lactide-co-glycolide), poly(hydroxybutyrate), poly(hydroxybutyrate-co-valerate), poly-orthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), and polyester amide. In more preferred embodiments, the polymer is poly(L)-lactic acid, poly(lactic-co-glycolic acid) (PLGA) or a combination of the two.

In specific embodiments, the composition further comprises a drug.

Another aspect of the invention contemplates a substrate that may be formulated for tissue culture and/or tissue engineering wherein the substrate is made of a composition as described herein above. In preferred embodiments, the substrate may further comprise a surface modification that allows cellular attachment. Preferably, the polymer of the invention employed as cell/tissue culture substrate is biodegradable. Preferably, the polymer also is biocompatible. The term "biocompatible" is intended to encompass a polymer that may be implanted in vivo or alternatively may be used for the growth of cells that may be implanted in vivo without producing an adverse reaction, such as an immunological response or otherwise altering the morphology of the cells grown thereon to render the cells incompatible with being implanted in vivo or used to model an in vivo organ.

Also contemplated herein is a method of producing engineered tissue, comprising providing a biodegradable composition of the present invention as a scaffold for the growth of cells and culturing cells of said tissue on the scaffold. In preferred methods, the polymer is composite of a poly 1,8-octanediol-co-citric acid, or a derivative thereof; or a poly 1,10-decanediol-co-citric acid or derivative thereof in combination with a biodegradable polymer such as PGLA or PLLA. In specific embodiments, the cells are selected from the group consisting of connective tissue cells, organ cells, muscle cells, nerve cells, and any combination thereof. In more specific embodiments, the cells are selected from the group consisting of tenocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, chondrocytes, and bone-forming cells. In other preferred embodiments, the tissue engineering method comprises growing the cells on the scaffold in a bioreactor.

In further embodiments, the compositions of the invention may be used as bandages, patches or sutures for implantation during surgery. In still other embodiments, the compositions of the present invention may be used to form a drug delivery device comprising a drug interspersed in the polymer composition of the invention.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIG. 4A-C: (A) Tensile strength, (B) Young's modulus, (C) Elongation at break of PLLA-PDC nanoscaffold composites and PDC control that were polymerized at 120° C. for 1 day with vacuum (n=4). (*p<0.01 from control).

FIG. 5A-C: SEM micrographs of (A) PLGA nanoparticles (Scale Bar=1 μm), (B) 5% PLGA-PDC nanocomposite (Scale Bar=2 μm), (C) 10% PLGA-PDC nanocomposite (Scale Bar=2 μm).

FIG. 6A-C: (A) Tensile strength, (B) Young's modulus, (C) Elongation at break of PLLA-PDC nanoscaffold composites and PDC control that were polymerized at 80° C. for 3 days without vacuum (n=4). (*p<0.01 from control).

DESCRIPTION OF THE PREFERRED EMBODIMENTS

Figure 1:
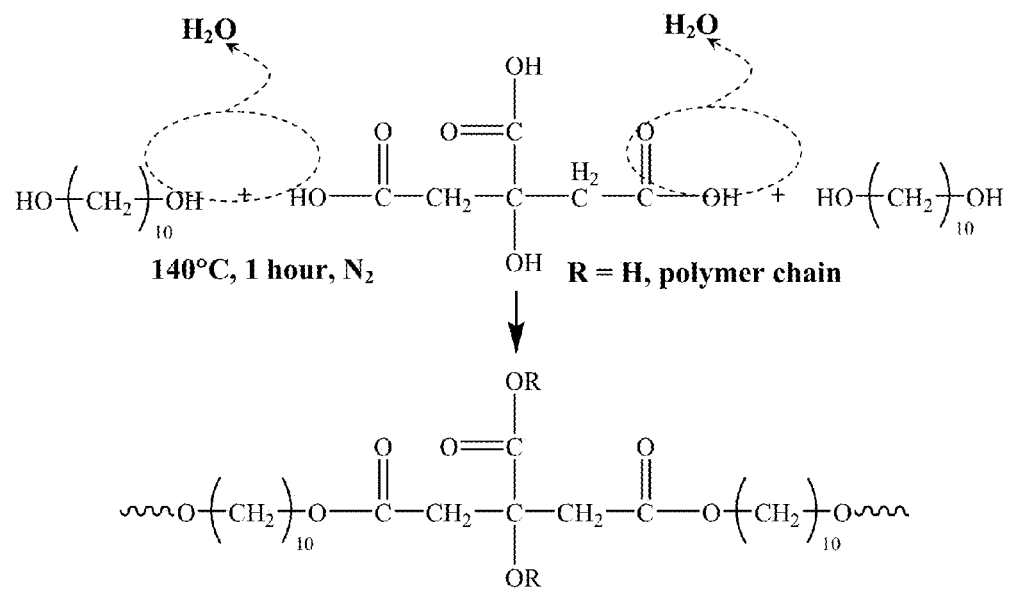
FIG. 1: Poly(diol citrate) reaction scheme.

Poly(diol citrates) are a family of biodegradable and biocompatible elastomers that have shown significant potential for soft tissue engineering. As noted above, it is desirable to increase the strength and stiffness while maintaining the ability to be elongated to many times their original length before rupture. The methods of the present invention are directed to strengthening such elastomers. One method by which elastomers can be strengthened and stiffened is by incorporating nanoparticles into the elastomeric matrix [2-4, 18]. This is case in the rubber industry where carbon black nanoparticles can be added to greatly increase the mechanical properties [2]. The nanoparticles act as additional crosslink points to reinforce the network chains and in general, the increase in mechanical properties is inversely proportional to the nanoparticle diameter [2].

Since poly(diol citrates) are targeted for soft tissue engineering, the nanophase used to reinforce the material must be made from a biodegradable and biocompatible polymer. Two polymers were chosen, poly(L-lactic acid) (PLLA) and poly(lactic-co-glycolic acid) (PLGA). These polymers were chosen as they are rigid and strong and have been used in many tissue engineering applications [19]. Furthermore, the rate of degradation could be tailored to match that of the surrounding elastomeric matrix. Poly(L-lactic acid) has a degradation time of greater than two years while poly (glycolic acid) has a degradation time of 1-2 months [20]. By changing the ratio of lactic to glycolic acid, the degradation rate could be varied from fast (1-2 months) to slow (>2 years). For tissue engineering, the rate of degradation of the polymer scaffold should match that of tissue regrowth.

Two methods were used to create biodegradable nanocomposites: (A) Nanoscaffolds of PLLA, (B) Nanoparticles of PLGA. The nanoscaffold method was chosen because it was believed that a rigid nano-fiber could scaffold could provide reinforcement to the material. Furthermore, a method to produce synthetic nanofibrous matrices was already developed elsewhere [21]. The nanoparticle method was chosen as it analogous to what is commonly done with elastomers to increase the mechanical properties of rubber [2-4, 18]. In addition, a simple method was found to produce large quantities of nanoparticles [22, 23]. Furthermore, it has been demonstrated that nanoparticles are a viable method by which drugs can be incorporated and released, thus allowing the possibility for drug release from nanocomposite materials [9-12]. These methods are exemplified in Example 2 below.

Thus, in order to enhance the mechanical properties of poly(diol citrates) nanocomposite materials were created using completely biodegradable and biocompatible polymers. This is the first report of nanocomposites for tissue engineering where the macro and nano phases are completely made from biodegradable and biocompatible synthetic co-polymers. Composites were created using nanoscaffolds and nanoparticles. The nanoparticle method is analogous to what is commonly done with rubber materials which are often doped with silica or carbon black nanoparticles to greatly increase their mechanical properties. However, because poly(diol citrates) are being targeted for tissue engineering, nondegradable carbon black or silica nanoparticles are not appropriate for the reinforcing nanophase. Poly(L-lactic acid) and poly(lactic-co-glycolic acid), two commonly used polymers for tissue engineering were used. These polymers were selected for their biocompatibility, rigid mechanical properties, and ease of fabrication into nanoscaffolds and nanoparticles. Creation of nanocomposites significantly increased the tensile strength and modulus compared to control materials. In particular, it should be noted that the tensile strength and elongation at break of the most preferred compositions of the present invention are greater than the strength and elongation at break of either of the polymer components individually. Since the materials are fabricated from two biodegradable and biocompatible materials, it is believed that the resulting nanocomposites could be used for tissue engineering applications. Furthermore, drug encapsulation and release has from nanoparticles has been demonstrated, thus raising the possibility of drug release from nanocomposites.

In preferred embodiments, the compositions of the present invention can be reinforced with a biocompatible, biodegradable mesh reinforcement component and/or with a three dimensional matrix comprised of nanofibers. The compositions of the present invention are such that they have a tensile strength and elasticity that is similar to soft tissue. For example, the compositions of the invention are prepared from a nanostructure that could be mesh or nanofiber matrix that has a tensile strength similar to that of human cartilage, human coronary arteries, or human ligament. As used herein, the term "nano-structure" is intended to encompass an object with at least one characteristic length between about 10 nm and about 500 nm. In specific embodiments of the invention, the biodegradable polymeric nanostructure is a nanoparticle. In a preferred embodiment the nano-structure is a nanofiber. In the most preferred embodiment, the nano-structure is a nanofibrillar network. Uses for such networks are described in for example, U.S. Pat. Nos. 6,599,323 and 6,146,892 (each incorporated herein by reference).

The compositions described herein in some aspects comprise a biodegradable elastomeric polymeric component and a biodegradable polymeric nano-structure. In certain embodiments, the nanocomposites of the invention are comprised of poly(diol citrate) molecules and a polymer that strengthens the poly(diol citrate) matrix. The polymer may be a biodegradable polymer or a non-biodegradable polymer, but preferably is a biodegradable polymer. Biodegradable polymers include, but are not limited to collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextran and derivatives, polysaccharides, poly(caprolactone), fibrinogen, poly(hydroxyl acids), poly(L-lactide) poly (D,L lactide), poly(D,L-lactide-co-glycolide), poly(L-lactide-co-glycolide), copolymers of lactic acid and glycolic acid, copolymers of .epsilon.-caprolactone and lactide, copolymers of glycolide and .epsilon.-caprolactone, copolymers of lactide and 1,4-dioxane-2-one, polymers and copolymers that include one or more of the residue units of the monomers D-lactide, L-lactide, D,L-lactide, glycolide, .epsilon.-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly (ethylene terephthalate), poly(malic acid), poly(tartronic acid), polyanhydrides, polyphosphazenes, poly(amino acids). The biodegradeable polymers used herein may be copolymers of the above polymers as well as blends and combinations of the above polymers. (see generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986).

In particular preferred embodiments, the biodegradable or resorbable polymer is one that is formed from one or more monomers selected from the group consisting of lactide, glycolide, e-caprolactone, trimethylene carbonate, 1,4-dioxan-2-one, 1,5-dioxepan-2-one, 1,4-dioxepan-2-one, hydroxyvalerate, and hydroxybutyrate. In one aspect, the polymer may include, for example, a copolymer of a lactide and a glycolide. In another aspect, the polymer includes a poly(caprolactone). In yet another aspect, the polymer includes a poly(lactic acid), poly(L-lactide)/poly(D,-L-Lactide) blends or copolymers of L-lactide and D,L-lactide. In yet another aspect, the polymer includes a copolymer of lactide and e-caprolactone. In yet another aspect, the polymer includes a polyester (e.g., a poly(lactide-co-glycolide). The poly(lactide-co-glycolide) may have a lactide:glycolide ratio ranges from about 20:80 to about 2:98, a lactide:glycolide ratio of about 10:90, or a lactide:glycolide ratio of about 5:95. In one aspect, the poly(lactide-co-glycolide) is poly(L-lactide-co-glycolide; see e.g., U.S. Pat. No. 6,531, 146 and U.S. application No. 2004/0137033.). Other examples of biodegradable materials include polyglactin, and polyglycolic acid.

Representative examples of non-biodegradable compositions include ethylene-co-vinyl acetate copolymers, acrylic-based and methacrylic-based polymers (e.g., poly(acrylic acid), poly(methylacrylic acid), poly(methylmethacrylate), poly(hydroxyethyl methacrylate), poly(alkylcynoacrylate), poly(alkyl acrylates), poly(alkyl methacrylates)), polyolefins such as poly(ethylene) or poly(propylene), polyamides (e.g., nylon 6,6), poly(urethanes) (e.g., poly(ester urethanes), poly(ether urethanes), poly(carbonate urethanes), poly(ester-urea)), polyesters (e.g., PET, polybutyleneterephthalate, and polyhexyleneterephthalate), olyethers (poly(ethylene oxide), poly(propylene oxide), poly(ethylene oxide)-poly(propylene oxide) copolymers, diblock and triblock copolymers, poly(tetramethylene glycol)), silicone containing polymers and vinyl-based polymers (polyvinylpyrrolidone, poly(vinyl alcohol), poly(vinyl acetate phthalate), poly(styrene-co-isobutylene-co-styrene), fluorine containing polymers (fluoropolymers) such as fluorinated ethylene propylene (FEP) or polytetrafluoroethylene (e.g., expanded PTFE).

The polymers may be combinations of biodegradable polymers, and also may be combinations of biodegradable and non-biodegradable polymers. Further examples of polymers that may be used are either anionic (e.g., alginate, carrageenin, hyaluronic acid, dextran sulfate, chondroitin sulfate, carboxymethyl dextran, caboxymethyl cellulose and poly(acrylic acid)), or cationic (e.g., chitosan, poly-I-lysine, polyethylenimine, and poly(allyl amine)) (see generally, Dunn et al., J. Applied Polymer Sci. 50:353, 1993; Cascone et al., J. Materials Sci.: Materials in Medicine 5:770, 1994; Shiraishi et al., Biol. Pharm. Bull. 16:1164, 1993; Thacharodi and Rao, Int'l J. Pharm. 120:115, 1995; Miyazaki et al., Int'l J. Pharm. 118:257, 1995). Preferred polymers (including copolymers and blends of these polymers) include poly(ethylene-co-vinyl acetate), poly(carbonate urethanes), poly(hydroxyl acids) (e.g., poly(D,L-lactic acid) oligomers and polymers, poly(L-lactic acid) oligomers and polymers, poly(D-lactic acid) oligomers and polymers, poly(glycolic acid), copolymers of lactic acid and glycolic acid, copolymers of lactide and glycolide, poly(caprolactone), copolymers of lactide or glycolide and ε-caprolactone), poly(valerolactone), poly(anhydrides), copolymers prepared from caprolactone and/or lactide and/or glycolide and/or polyethylene glycol.

In specific embodiments, the compositions of the invention (i.e., the compositions that are made up of a poly(diol citrate) polymer and a polymer that stiffens the poly diol citrate polymer) are molded or otherwise formed into flexible compositions that can be used as "patches." Such "patches" may be comprises of just the poly(diol citrate) polymer and a polymer, or they may be impregnated or otherwise loaded with a drug or other biologically active agent to be delivered (e.g., in a controlled-release manner) or they may be seeded with cells so that they can act as cellular tissue patches or tissue grafts.

In specific embodiments, the elastomeric composites made according to the methods of the present invention will be useful both as substrata for the growth and propagation of tissues cells that may be seeded on the substrata and also as implantable devices. In those embodiments where the elastomeric composites are used as bioimplantable devices, the substrate may be formulated into a shape suitable for implantation. For example, as described in U.S. Pat. No. 6,423,092 (incorporated herein by reference), it may be desirable to fabricate a biodegradable stent for implantation into a lumen. The composites of the invention may also be used in craniofacial applications, for example, as an alternative to spring-mediated cranial reshaping for the treatment of craniosynostosis [27]. In certain embodiments of the invention, it may be desirable to produce prosthetic organ tissue for implantation into an animal, such as e.g., testicular tissue described in U.S. Pat. No. 6,620,203 (incorporated herein by reference). Other organs for which tissue implantation patches may be generated include, but are not limited to skin tissue for skin grafts, myocardial tissue, bone tissue for bone regeneration, testicular tissue, endothelial cells, blood vessels, and any other cells from which a tissue patch may be generated. Thus, those of skill in the art would understand that the aforementioned organs/cells are merely exemplary organs/cell types and it should be understood that cells from any organ may be seeded onto the biocompatible elastomeric composites of the invention to produce useful tissue for implantation and/or study.

The cells that may be seeded onto the elastomeric composites of the present invention may be derived from commercially available cell lines, or alternatively may be primary cells, which can be isolated from a given tissue by disaggregating an appropriate organ or tissue which is to serve as the source of the cells being grown. This may be readily accomplished using techniques known to those skilled in the art. Such techniques include disaggregation through the use of mechanically forces either alone or in combination with digestive enzymes and/or chelating agents that weaken cell-cell connections between neighboring cells to make it possible to disperse the tissue into a suspension of individual cells without appreciable cell breakage. Enzymatic dissociation can be accomplished by mincing the tissue and treating the minced tissue with any of a number of digestive enzymes either alone or in combination. Digestive enzymes include but are not limited to trypsin, chymotrypsin, collagenase, elastase, and/or hyaluronidase, Dnase, pronase, etc. Mechanical disruption can also be accomplished by a number of methods including, but not limited to the use of grinders, blenders, sieves, homogenizers, pressure cells, or sonicators to name but a few. For a review of tissue disaggregation techniques, see Freshney, Culture of Animal Cells. A Manual of Basic Technique, 2d Ed., A. R. Liss, Inc., New York, 1987, Ch. 9, pp. 107-126.

Once the primary cells are disaggregated, the cells are separated into individual cell types using techniques known to those of skill in the art. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137-168. Media and buffer conditions for growth of the cells will depend on the type of cell and such conditions are known to those of skill in the art.

In certain embodiments, it is contemplated that the cells attached to the biocompatible elastomeric composite substrates of the invention are grown in bioreactors. A bioreactor may be of any class, size or have any one or number of desired features, depending on the product to be achieved. Different types of bioreactors include tank bioreactors, immobilized cell bioreactors, hollow fiber and membrane bioreactors as well as digesters. There are three classes of immobilized bioreactors, which allow cells to be grown: membrane bioreactors, filter or mesh bioreactors, and carrier particle systems. Membrane bioreactors grow the cells on or behind a permeable membrane, allowing the nutrients to leave the cell, while preventing the cells from escaping. Filter or mesh bioreactors grow the cells on an open mesh of an inert material, allowing the culture medium to flow past, while preventing the cells from escaping. Carrier particle systems grow the cells on something very small, such as small nylon or gelatin beads. The bioreactor can be a fluidized bed or a solid bed. Other types of bioreactors include pond reactors and tower fermentors. Any of these bioreactors may be used in the present application for regenerating/engineering tissues on the citric acid based elastomeric composites of the present invention.

Certain tissues that are regenerated by use of the citric acid based elastomeric composites of the invention may be encapsulated so as to allow the release of desired biological materials produced by the cells at the site of implantation, while sequestering the implanted cells from the surrounding site. Cell encapsulation can be applied to all cell types secreting a bioactive substance either naturally or through genetic engineering means. In practice, the main work has been performed with insulin secreting tissue.

Encapsulation procedures are most commonly distinguished by their geometrical appearance, i.e. micro- or macro-capsules. Typically, in microencapsulation, the cells are sequestered in a small permselective spherical container, whereas in macroencapsulation the cells are entrapped in a larger non-spherical membrane, Lim et al. (U.S. Pat. Nos. 4,409,331 and 4,352,883) discloses the use of microencapsulation methods to produce biological materials generated by cells in vitro, wherein the capsules have varying permeabilities depending upon the biological materials of interest being produced, Wu et al, Int. J. Pancreatology, 3:91-100 (1988), disclose the transplantation of insulin-producing, microencapsulated pancreatic islets into diabetic rats.

As indicated above, the cells that are seeded on the elastomeric composites of the present invention may be cell lines or primary cells. In certain preferred embodiments, the cells are genetically engineered cells that have been modified to express a biologically active or therapeutically effective protein product. Techniques for modifying cells to produce the recombinant expression of such protein products are well known to those of skill in the art. In particular preferred embodiments, the compositions of the invention may be used to form of a tissue graft or tissue patch. Such a tissue graft may be an autograft, allograft, biograft, biogenic graft or xenograft. Tissue grafts may be derived from various tissue types. Representative examples of tissues that may be used to prepare biografts include, but are not limited to, rectus sheaths, peritoneum, bladder, pericardium, veins, arteries, diaphragm and pleura. For such grafts the cells may be endothelial cells, ligament tissue, muscle cells, bone cells, cartilage cells. Such cells may be grafted into the compositions of the invention alone or in combination with a drug or biologically active agent to be delivered to an in vivo site. For example, such cells for the biograft may be harvested from a host, loaded with the agent of interest and then applied in a perivascular manner at the site where lesions and intimal hyperplasia can develop. Once implanted, the agent of interest (e.g., paclitaxel) is released from the graft and can penetrate the vessel wall to prevent the formation of intimal hyperplasia at the treatment site. In certain embodiments, the biograft may be used as a backing layer to enclose a composition (e.g., a gel or paste loaded with anti-scarring agent).

The patches made of the compositions of the present invention may be combined with drugs for delivery or therapeutic agents that can form part of a tissue patch prepared from the polymers of the invention. For example, the compositions of the invention may be used to form a mesh or a patch made of the biodegradable polymeric matrix that conforms to the tissue and releases the agent (e.g., a therapeutic agent such as a drug or a diagnostic agent such as a marker, dye or other marker of that will allow visualization of a diseased state). In preferred examples, the compositions are fashioned into a mesh or patch that incorporates a drug that can be released in a controlled release manner. See, e.g., U.S. Pat. No. 6,461,640. The mesh or patch made of the compositions of the invention may be impregnated with an antioxidant and/or antimicrobial. See, e.g., U.S. Pat. No. 6,572,878. The mesh or patch may be a tissue patch that is adapted to cover a bony dissection in the spine. See, e.g., U.S. Pat. No. 5,868,745 and U.S. patent application No. 2003/0078588. The tissue patch made of the compositions of the invention may be prepared to be wrapped around a nerve in a canal to reduce fibroplasia. See, e.g., U.S. Pat. No. 6,106,558. The tissue patch may be a resorbable collagen membrane that is wrapped around the spinal chord to inhibit cell adhesions. See, e.g., U.S. Pat. No. 6,221,109. The tissue patch may be used as a dressing to cover a wound and promote wound healing. See, e.g., U.S. Pat. No. 6,548,728. The compositions of the present invention may be prepared as a bandage that contains a scar treatment pad with a layer of silicone elastomer or silicone gel. See, e.g., U.S. Pat. Nos. 6,284,941 and 5,891,076. The compositions may be used to incorporate a biologically active compound. See, e.g., U.S. Pat. Nos. 6,323,278; 6,166, 130; 6,051,648 and 5,874,500.

Methods for incorporating the a biologically active material onto or into the mesh or patch of the invention include: (a) affixing (directly or indirectly) to the patch such a biologically active material (e.g., by either a spraying process or dipping process as described above, with or without a carrier), (b) incorporating or impregnating into the patch made with the composition with a biologically active material (e.g., by either a spraying process or dipping process as described above, with or without a carrier (c) by coating the patch made with the composition with a substance such as a hydrogel which will in turn absorb the biologically active material, (d) constructing the patch made with the composition itself with the biologically active material in either the biodegradable polymer, the poly(diol citrate) polymer, or in the mixture of the two, or (e) by covalently binding the biologically active material directly to the surface of the composition of the invention.

The compositions of the present invention also may be used to coat devices such as medical stents and the like. For devices that are coated, the coating process can be performed in such a manner as to (a) coat only one surface of device with the compositions of the invention or (b) coating all or parts of the device with the compositions of the invention.

The nanocomposites of the present invention also will be useful in soft tissue engineering as described in the examples herein below.

The patches prepared from the compositions of the invention or a device coated with the same may be made sterile either by preparing them under aseptic environment and/or they may be terminally sterilized using methods known in the art, such as gamma radiation or electron beam sterilization methods or a combination of both of these methods.

Patches made with the compositions of the invention may be applied to any bodily conduit or any tissue. Prior to implantation, the patch may be trimmed or cut from a sheet of bulk material to match the configuration of the widened foramen, canal, or dissection region, or at a minimum, to overlay the exposed tissue area. Such a patch may be shaped to match the particular configuration of the placement region. For example, the patch may be rolled in a cuff shape or cylindrical shape and placed around the exterior periphery of the desired tissue. It may be provided in a relatively large bulk sheet and then cut into shapes to mold the particular structure and surface topography of the tissue or device to be wrapped. Alternatively, it may be pre-shaped into one or more patterns for subsequent use. The patches made from the compositions of the invention may be typically rectangular in shape and be placed at the desired location within the surgical site by direct surgical placement or by endoscopic techniques. The patches may be secured into place by wrapping it onto itself (i.e., self-adhesive), or by securing it with sutures, staples, sealant, and the like. Alternatively, the film or mesh may adhere readily to tissue and therefore, additional securing mechanisms may not be required.

The patches made from the compositions of the invention may be used for a variety of indications, including, without limitation: (a) prevention of surgical adhesions between tissues following surgery (e.g., gynecologic surgery, vasovasostomy, hernia repair, nerve root decompression surgery and laminectomy); (b) prevention of hypertrophic scars or keloids (e.g., resulting from tissue burns or other wounds); (c) prevention of intimal hyperplasia and/or restenosis (e.g., resulting from insertion of vascular grafts or hemodialysis access devices); (d) may be used in affiliation with devices and implants that lead to scarring as described herein (e.g., as a sleeve or mesh around a breast implant to reduce or inhibit scarring); (e) prevention of infection (e.g., resulting from tissue burns, surgery or other wounds); or (f) may be used in affiliate with devices and implants that lead to infection as described herein.

The patches made of the compositions of the invention may be used for hernia repair surgery or in other types of surgical procedures as discussed in U.S. Pat. Nos. 6,638,284; 5,292,328; 4,769,038 and 2,671,444. Thus, the patches made from the compositions of the invention also may be used to prepare hernia meshes, which support the repaired hernia or other body structures during the healing process. Hernias are often repaired surgically to prevent complications. Conditions in which a hernia mesh may need to be used include, without limitation, the repair of inguinal (i.e., groin), umbilical, ventral, femoral, abdominal, diaphragmatic, epigastric, gastroesophageal, hiatal, intermuscular, mesenteric, paraperitoneal, rectovaginal, rectocecal, uterine, and vesical hernias. Hernia repair typically involves returning the viscera to its normal location and the defect in the wall is primarily closed with sutures, but for bigger gaps, a mesh is placed over the defect to close the hernia opening. Infiltration of the subject polymer composition comprising an anti-scarring agent into tissue adjacent to a hernia repair mesh may reduce or prevent fibrosis proximate to the implanted hernia mesh, thereby minimizing the possibility of adhesions between the abdominal wall or other tissues and the mesh itself, and reducing further complications and abdominal pain.

In yet another aspect, the patches made from the compositions of the invention may be used for delivering a specific therapeutic or other agent to an external portion (surface) of a body passageway or cavity. Examples of body passageways include arteries, veins, the heart, the esophagus, the stomach, the duodenum, the small intestine, the large intestine, biliary tracts, the ureter, the bladder, the urethra, lacrimal ducts, the trachea, bronchi, bronchiole, nasal airways, Eustachian tubes, the external auditory mayal, vas deferens and fallopian tubes. Examples of cavities include the abdominal cavity, the buccal cavity, the peritoneal cavity, the pericardial cavity, the pelvic cavity, perivisceral cavity, pleural cavity and uterine cavity.

In the following Examples, Example 1 is directed to teachings of methods of producing various poly(diol) citrate molecules. Example 2 provides teachings of how to strengthen and stiffen biocompatible membranes made from such poly(diol) citrate molecules. These nanocomposite materials described herein can be used in tissue engineering, drug delivery, or any application where strong biodegradable and flexible elastomeric materials may be necessary. The increasing and fast development of tissue engineering applications will require this type of technology to maximize flexibility for design requirements of scaffolds for tissue engineering or drug delivery devices.

EXAMPLE 1

Biodegradable Elastomeric Polymers

The nanoparticle compositions of the invention are based on biodegradable elastomeric polymers of poly(diol) citrate molecules. Such molecules typically comprising a polyester network of citric acid copolymerized with a linear aliphatic di-OH monomer in which the number of carbon atoms ranges from 2 to 20. Polymer synthesis conditions for the preparation of these molecules vary from mild conditions, even at low temperature (less than 100° C.) and no vacuum, to tough conditions (high temperature and high vacuum) according the requirements for the materials properties. By changing the synthesis conditions (including, but not limited to, post-polymerization temperature, time, vacuum, the initial monomer molar ratio, and the di-OH monomer chain length) the mechanical properties of the polymer can be modulated over a wide range. This series of polymers exhibit a soft, tough, biodegradable, hydrophilic properties and excellent biocompatibility in vitro.

The poly(diol)citrate polymers used herein have a general structure of:

$$(A-B-C)_n$$

Where A is a linear, aliphatic diol and C also is a linear aliphatic diol. B is citric acid. The citric acid co-polymers of the present invention are made up of multiples of the above formula, as defined by the integer n, which may be any integer greater than 1. It is contemplated that n may range from 1 to about 1000 or more. It is particularly contemplated that n may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 31, 32, 33, 34, 35, 36, 37, 38, 39, 40, 41, 42, 43, 44, 45, 46, 47, 48, 49, 50, or more.

In preferred embodiments, the identity of "A" above is poly 1,10-decanediol and in another preferred embodiment the identity of A is 1,8-octanediol. However, it should be understood that this is merely an exemplary linear, aliphatic diol. Those of skill are aware of other aliphatic alcohols that will be useful in polycondensation reactions to produce poly citric acid polymers. Exemplary such aliphatic diols include any diols of between about 2 carbons and about 20 carbons. While the diols are preferably aliphatic, linear, unsaturated diols, with the hydroxyl moiety being present at the $C_1$ and $C_x$ position (where x is the terminal carbon of the diol), it is contemplated that the diol may be an unsaturated diol in which the aliphatic chain contains one or more double bonds. The preferred identity for "C" in one embodiment is 1,8, octanediol, however as with moiety "A," "C" may be any other aliphatic alcohols. While in specific embodiments, both A and C are both the same diol, e.g., 1,8-octanediol, it should be understood that A and C may have different carbon lengths. For example, A may be 2, 3, 4, 5, 6, 7, 8, 9, 10, 11, 12, 13, 14, 15, 16, 17, 18, 19, 20 or more carbons in length, and C may independently be 2, 3, 4, 5, 6, 7, 8, 9, 10, 11, 12, 13, 14, 15, 16, 17, 18, 19, 20 or more carbons in length. Exemplary methods for the polycondensation of the citric acid with the linear diols are provided in this Example. These materials are then used as starting materials for the composites described in Example 2.

Synthesis of Poly(1,10-decanediol-co-citric acid) (PDC) In a typical experiment, 19.212 g citric acid and 17.428 g 1,10-decanediol were added to a 250 ml three-neck round-bottom flask, fitted with an inlet adapter and an outlet adapter. The mixture was melted within 15 min by stirring at 160-165° C. in silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 60° C., 80° C. or 120° C. with and without vacuum for predetermined time from one day to 3 weeks depending on the temperature to achieve the Poly(1,10-decanediol-co-citric acid). Nitrogen was introduced into the reaction system before the polymer was taken out from reaction system.

Preparation of Poly(1,8-Octanediol-co-citric acid) (POC) In a typical experiment, 19.212 g citric acid and 14.623 g Octanediol were added to a 250 mL three-neck round-bottom flask, fitted with an inlet adapter and an outlet adapter. The mixture was melted within 15 min by stirring at 160-165° C. in silicon oil bath, and then the temperature of the system was lowered to 140° C. The mixture was stirred for another 1 hr at 140° C. to get the pre-polymer. Nitrogen was vented throughout the above procedures. The pre-polymer was post-polymerized at 60° C., 80° C. or 120° C. with and without vacuum for predetermined time (from one day to 3 weeks depending on the temperature, with the lower temperatures requiring longer times) to achieve the Poly(1,8-octanediol-co-citric acid). Nitrogen was introduced into the reaction system before the polymer was taken out from reaction system.

Porous scaffolds of POC (tubular and flat sheets) were prepared via a salt leaching technique as follows: POC pre-polymer was dissolved into dioxane to form 25 wt % solution, and then the sieved salt (90-120 microns) was added into pre-polymer solution to serve as a porogen. The resulting slurry was cast into a poly(tetrafluoroethylene) (PTFE) mold (square and tubular shape). After solvent evaporation for 72 h, the mold was transferred into a vacuum oven for post-polymerization. The salt in the resulting composite was leached out by successive incubations in water (produced by Milli-Q water purification system every 12 h for a total 96 h. The resulting porous scaffold was air-dried for 24 hr and then vacuum dried for another 24 hrs. The resulting scaffold was stored in a dessicator under vacuum before use. Porous scaffolds are typically preferred when cells are expected to migrate through a 3-dimensional space in order to create a tissue slice. Solid films would be used when a homogenous surface or substrate for cell growth is required such as an endothelial cell monolayer within the lumen of a vascular graft.

Using similar techniques porous scaffold of PDC or other poly(diol)citrates can be prepared.

Synthesis of Poly(1,6-hexanediol-co-citric acid) (PHC) In a typical experiment, 19.212 g citric acid and 11.817 g 1,6-hexanediol were added to a 250 ml three-neck round-bottom flask, fitted with an inlet adapter and an outlet adapter. The mixture was melted within 15 min by stirring at 160-165° C. in a silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 60° C., 80° C. or 120° C. with and without vacuum for a predetermined time from one day to 3 weeks, depending on the temperature, to achieve the Poly(1,6-hexanediol-co-citric acid). Nitrogen was introduced into the reaction system before the polymer was taken out from reaction system.

Synthesis of Poly(1,12-dodecanediol-co-citric acid) PDDC. In a typical experiment, 19.212 g citric acid and 20.234 g 1,12-dodecanediol were added to a 250 ml three-neck round-bottom flask, fitted with an inlet adapter and an outlet adapter. The mixture was melted within 15 min by stirring at 160-165° C. in silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 60° C., 80° C. or 120° C. with and without vacuum for predetermined time from one day to 3 weeks depending on the temperature to achieve the Poly(1,12-dodecanediol-co-citric acid). Nitrogen was introduced into the reaction system before the polymer was taken out from reaction system.

Synthesis of Poly(1,8-octanediol-co-citric acid-co-glycerol) In a typical experiment (Poly(1,8-octanediol-co-citric acid-co-1% glycerol), 23.0544 g citric acid, 16.5154 g 1,8-octanediol and 0.2167 g glycerol were added to a 250 ml three-neck round-bottom flask, fitted with an inlet adapter and an outlet adapter. The mixture was melted within 15 min by stirring at 160-165° C. in silicon oil bath, and then the temperature of the system was lowered to 120° C. The mixture was stirred for another hour at 140° C. to get the pre-polymer. Nitrogen was vented throughout the above procedures. The pre-polymer was post-polymerized at 60° C., 80° C. or 120° C. with and without vacuum for predetermined time from one day to 3 weeks depending on the temperature to achieve the Poly(1,8-octanediol-co-citric acid-co-1% glycerol). Nitrogen was introduced into the reaction system before the polymer was taken out from reaction system.

Synthesis of Poly(1,8-octanediol-citric acid-co-polyethylene oxide). In a typical experiment, 38.424 g citric acid, 14.623 g 1,8-octanediol and 40 g polyethylene oxide with molecular weight 400 (PEO400) (100 g PEO1000 and 200 g PEO2000 respectively) (molar ratio: citric acid/1,8-octanediol/PEO400=1/0.5/0.5) were added to a 250 ml or 500 ml three-neck round-bottom flask, fitted with an inlet adapter and an outlet adapter. The mixture was melted within 15 min by stirring at 160-165° C. in silicon oil bath, and then the temperature of the system was lowered to 135° C. The mixture was stirred for 2 hours at 135° C. to get the pre-polymer. Nitrogen was vented throughout the above procedures. The pre-polymer was post-polymerized at 120° C. under vacuum for predetermined time from one day to 3 days to achieve the Poly(1,8-octanediol-citric acid-co-polyethylene oxide). Nitrogen was introduced into the reaction system before the polymer was taken out from reaction system. The molar ratios can be altered to achieve a series of polymers with different properties.

Synthesis of Poly(1,12-dodecanediol-citric acid-co-polyethylene oxide). In a typical experiment, 38.424 g citric acid, 20.234 g 1,12-dodecanediol and 40 g polyethylene oxide with molecular weight 400 (PEO400) (100 g PEO1000 and 200 g PEO2000 respectively) (molar ratio: citric acid/1,8-octanediol/PEO400=1/0.5/0.5) were added to a 250 ml or 500 ml three-neck round-bottom flask, fitted with an inlet adapter and an outlet adapter. The mixture was melted within 15 min by stirring at 160-165° C. in silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 120° C. under vacuum for predetermined time from one day to 3 days to achieve the Poly(1,12-dodecanediol-citric acid-co-polyethylene oxide). Nitrogen was introduced into the reaction system before the polymer was taken out from reaction system. The molar ratios can be altered to achieve a series of polymers with different properties.

Synthesis of Poly(1,8-octanediol-citric acid-co-N-methyldiethanoamine) POCM. In a typical experiment, 38.424 g citric acid, 26.321 g 1,8-octanediol and 2.3832 g N-methyldiethanoamine (MDEA) (molar ratio: citric acid/1,8-octanediol/MDEA=1/0.90/0.10) were added to a 250 ml or 500 ml three-neck round-bottom flask, fitted with an inlet adapter and an outlet adapter. The mixture was melted within 15 min by stirring at 160-165° C. in silicon oil bath, and then the temperature of the system was lowered to 13520° C. The mixture was stirred for half an hour at 120° C. to get the pre-polymer. Nitrogen was vented throughout the above procedures. The pre-polymer was post-polymerized at 80° C. for 6 hours, 120° C. for 4 hours without vacuum and then 120° C. for 14 hours under vacuum to achieve the Poly(1,8-octanediol-citric acid-co-N-methyldiethanoamine) Nitrogen was introduced into the reaction system before the polymer was taken out from reaction system. The molar ratios can be altered to citric acid/1,8-octanediol/MDEA=1/0.95/0.05.

Synthesis of Poly(1,12-dodecanediol-citric acid-co-N-methyldiethanoamine) PDDCM. In a typical experiment, 38.424 g citric acid, 36.421 g 1,12-dodecanediol and 2.3832 g N-methyldiethanoamine (MDEA) (molar ratio: citric acid/1,8-octanediol/MDEA=1/0.90/0.10) were added to a 250 ml or 500 ml three-neck round-bottom flask, fitted with an inlet adapter and an outlet adapter. The mixture was melted within 15 min by stirring at 160-165° C. in a silicon oil bath, and then the temperature of the system was lowered to 120° C. The mixture was stirred for half an hour at 120° C. to get the pre-polymer. Nitrogen was vented throughout the above procedures. The pre-polymer was post-polymerized at 80° C. for 6 hours, 120° C. for 4 hours without vacuum and then 120° C. for 14 hours under vacuum to achieve the Poly(1,12-dodecanediol-citric acid-co-N-methyldiethanoamine) Nitrogen was introduced into the reaction system before the polymer was taken out from reaction system. The molar ratios can be altered to citric acid/1,12-dodecanediol/MDEA=1/0.95/0.05.

EXAMPLE 2

Biodegradable Elastomeric Composites Made from Biodegradable Elastomeric Polymers Example 1 describes the production of PDC as well as a number of other poly(diol)citrate polymers. In the present Example, there are provided teachings of how to further strengthen and stiffen the composite by incorporating nanoparticles into the elastomeric polymer matrix [2-4, 18]. The nanoparticles act as additional crosslink points to reinforce the network chains and in general, the increase in mechanical properties is inversely proportional to the nanoparticle diameter [2]. The exemplary polymers chosen for the nanophase were poly(L-lactic acid) (PLLA) and poly(lactic-co-glycolic acid) (PLGA). These polymers were chosen as they are rigid and strong and have been used in many tissue engineering applications [19]. Furthermore, the rate of degradation could be tailored to match that of the surrounding elastomeric matrix. Poly(L-lactic acid) has a degradation time of greater than two years while poly(glycolic acid) has a degradation time of 1-2 months [20]. By changing the ratio of lactic to glycolic acid, the degradation rate could be varied from fast (1-2 months) to slow (>2 years). For tissue engineering, the rate of degradation of the polymer scaffold should match that of tissue regrowth.

Materials & Methods

Poly(Diol Citrate) Pre-Polymer Synthesis: Citric acid and 1,10-decanediol were melted under a flow of nitrogen gas by stirring at 165° C. in a silicon oil bath and then stirred for another hour at 140° C. to create a pre-polymer solution, poly(1,10-decanediol-co-citrate) (PDC). The mechanism of PDC synthesis is shown in FIG. (1) below. For nanoscaffold composite preparation, the PDC prepolymer was dissolved in ethanol to a concentration of 30%. For nanoparticle composite preparation, PDC was dissolved in 1,4-dioxane to a concentration of 25%.

Nanoscaffold Synthesis: Poly(L-lactic acid) (PLLA) nanoscaffolds were prepared using a thermally induced gelation, solvent exchange, and freeze drying method [21]. PLLA (Mw~50,000, polydispersity~1.8) was dissolved in tetrahydrofuran (THF) to make solutions with concentrations of 2.5%, 5%, and 10%. The PLLA solution was cast into a Teflon Petri dish and immediately placed into a ~80° C. freezer for 1 hour to induce gelation. The gel was then transferred to a −20° C. freezer for 1 hour. After 1 hour, the dish containing the gel was removed from the ~20° C. freezer and immersed in a large volume of water for solvent exchange. The water was changed 3 times per day for two days ensure complete removal of solvent. The gel was removed from the water, blotted dry with filter paper, and freeze-dried for 2 days using a Freezone-6 lyophilizer (Labconco, Kansas City, Mo.).

Nanoscaffold Composite Synthesis: Freeze-dried nanoscaffolds were transferred to a Teflon Petri dish and PDC prepolymer in ethanol was poured over the nanoscaffold. The dish was subjected to repeated vacuum/repressurization cycles to ensure the prepolymer filled the nanopores. Excess prepolymer was removed from the dish and the nanocomposite polymerized at 60° C. for 4 hours. Following this, the PDC prepolymer coating and vacuum/repressurization cycles was repeated one additional time to ensure that the pores were completely filled with polymer. After the final coating, the composite was polymerized at 120° C. for 1 day without vacuum followed by 120° C. for 1 day with vacuum.

Characterization of Nanoscaffolds: The density and porosity of the scaffold was measured using a method based on Archimedes' principle [24]. Briefly, a density bottle was filled with ethanol and weighed once equilibrated to 30° C. ($W_1$) in a water bath. The polymer scaffold of mass $W_s$ was then immersed in the density bottle and the air bubbles removed from the pores under vacuum. The bottle was supplemented with ethanol and weighed once again ($W_2$). The scaffold saturated with ethanol was removed from the bottle and the bottle weighed one final time ($W_3$). The density and porosity of the scaffolds were calculated using the following equations where $V_p$ is the volume of the scaffold pores, $V_s$ is the volume of the scaffold skeleton, $\rho_s$ is the scaffold density, and $\epsilon$ is the porosity.

$$V_p = \frac{(W_2 - W_3 - W_s)}{\rho_e} \quad (1)$$

$$V_s = \frac{(W_1 - W_2 + W_s)}{\rho_e} \quad (2)$$

$$\rho_s = \frac{W_s}{V_s} \quad (3)$$
$$= \frac{W_s \rho_e}{(W_1 - W_2 + W_s)}$$

$$\varepsilon = \frac{V_p}{(V_p + V_s)} \quad (4)$$
$$= \frac{(W_2 - W_3 - W_s)}{(W_1 - W_3)}$$

The morphology of the nanofibrous matrices and nanoscaffold composites were studied using an LEO 1525 scanning electron microscope (Zeiss, Thornwood, N.Y.). SEM images were analyzed using image analysis software (Image-Pro® Plus V.4.0, Silver Spring, Md.) to obtain the pore size and fiber diameter data. Over fifty measurements were averaged to get the mean value and standard deviation of the pore size.

Figure 2:
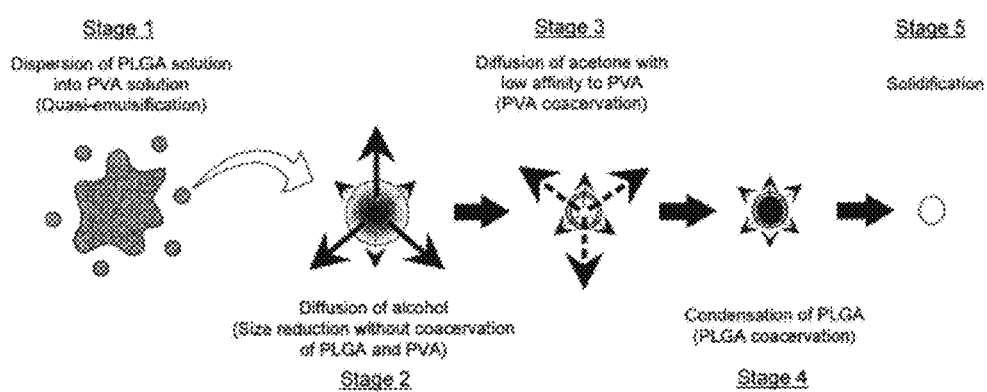
FIG. 2: PLGA Nanoparticle Formation.

Nanoparticle Preparation: Poly(lactic-co-glycolic acid) (PLGA) and Poly(L-lactic acid) nanoparticles were prepared using a modified spontaneous emulsion and solvent diffusion method [23, 25]. PLGA or PLLA was dissolved in a 60:40 acetone/ethanol mixture to form solutions with concentrations ranging from 1-4%. Poly(vinyl alcohol) (PVA) (80% hydrolyzed) was dissolved in ml of water to create a 4% (w/v) solution. The PLGA in solvent mixture was added dropwise to the PVA in water solution (1 part PLGA, 4 parts PVA) under high speed magnetic stirring to form nanoparticles. The nanoparticles in solution were concentrated to a volume of 300 ml using an Amicon 8400 ultrafiltration cell with polyethersulfone membrane (Mw~500,000) (Millipore, Billerica, Mass.) and then centrifuged at 48,400 g to pellet the nanoparticles. The supernatant was discarded and the tube washed several times with water before resuspending the particles in water. The mechanism of nanoparticle formation is shown in FIG. 2).

Nanoparticle Composite Synthesis: To create a nanocomposite, the nanoparticles were added to the prepolymer under magnetic stirring and the mixture quickly cast into a glass Petri dish. The amount of nanoparticles added was varied to create composites with 5% and 10% nanoparticles by weight. Water and 1,4-dioxane were removed by freeze drying for 1 week using a Freezone-6 lyophilizer (Labconco, Kansas City, Mo.). After removal of solvent and water, the dish transferred to an 80° C. oven for 3 days to finish polymerization.

Characterization of Nanoparticles: Recovery of nanoparticles after centrifugation was assessed by measuring the dry mass of the particles and comparing it to the mass of polymer used in the formulation. Nanoparticle diameters were assessed using dynamic light scattering. The morphology of the nanoparticles and nanocomposites were studied using an LEO 1525 scanning electron microscope (Zeiss, Thornwood, N.Y.). The amount of PVA on the surface of the nanoparticles was determined using the Alléman method [26]. Briefly, 200 mg of freeze dried nanoparticles were dissolved in 25 ml of chloroform with sonication for 30 minutes. The organic solution was filtered using a membrane filter and the residual PVA on the filter washed with a small volume of chloroform. The filter was dried under atmospheric pressure and then transferred to a 250 ml beaker. One hundred grams of purified water was added to the flask and heated to dissolve the PVA. After removing the filter and cooling, the weight of the PVA solution was adjusted to 100 g. Fifteen milliliters of a boric acid solution (4% w/w) and 3 ml of an iodine solution (1.27% (w/w) iodine and 2.5% (w/w) potassium iodide in purified water) were added 5 ml of the PVA solution. The volume was adjusted to 50 ml with water and the absorbance assayed spectrophotometrically ($\lambda$=620, 690 nm).

Mechanical Characterization of Polymers: Tensile tests using ASTM D412a with a modified sample size (26 mm×4 mm×1.5 mm) were performed on an Instron 5544 mechanical tester (Instron, Canton, Mass.) equipped with a 500N load cell. From these tests the ultimate tensile strength, Young's modulus, and elongation at break were recorded.

Statistical Methods: Data are expressed as means±standard deviation. The statistical significance between two sets of data was calculated using two-tail Student's t-test. Analysis of variance (ANOVA) and post-hoc analysis using the Tukey and Bonferoni tests were used to determine significant differences among three or more means. Data were taken to be significant, when a P-value of 0.05 or less was obtained.

Results & Discussion

Nanoscaffold Results

Three different nanoscaffolds were produced with 2.5%, 5%, or 10% PLLA. By varying the concentration of PLLA in tetrahydrofuran, the characteristics of the nanoscaffold could be adjusted. Table (1) shows the characteristics of the PLLA nanoscaffolds before the pores were filled with PDC. With increasing PLLA concentration, the density and fiber diameter increase, while the porosity and pore size decrease. A lower porosity decreases the amount of poly(diol citrate) macro-phase that can be incorporated into the composite. However, a lower porosity and greater fiber size result in a greater proportion of PLLA in the final nanocomposite.

TABLE (1)

Nanoscaffold Characteristics

|  | 2.5% PLLA | 5% PLLA | 10% PLLA |
|---|---|---|---|
| Fiber Diameter (nm) | 124.3 ± 27.3 | 246.3 ± 69.1 | 206.7 ± 70.4 |
| Density (g/cm$^3$) | 0.033 ± 0.007 | 0.063 ± 0.004 | 0.117 ± 0.006 |
| Porosity (%) | 97.37 ± 0.57 | 94.95 ± 0.32 | 90.56 ± 0.50 |
| Pore Size (nm) | 706.6 ± 266.1 | 643.8 ± 233.5 | 617.2 ± 362.9 |

Figure 3:
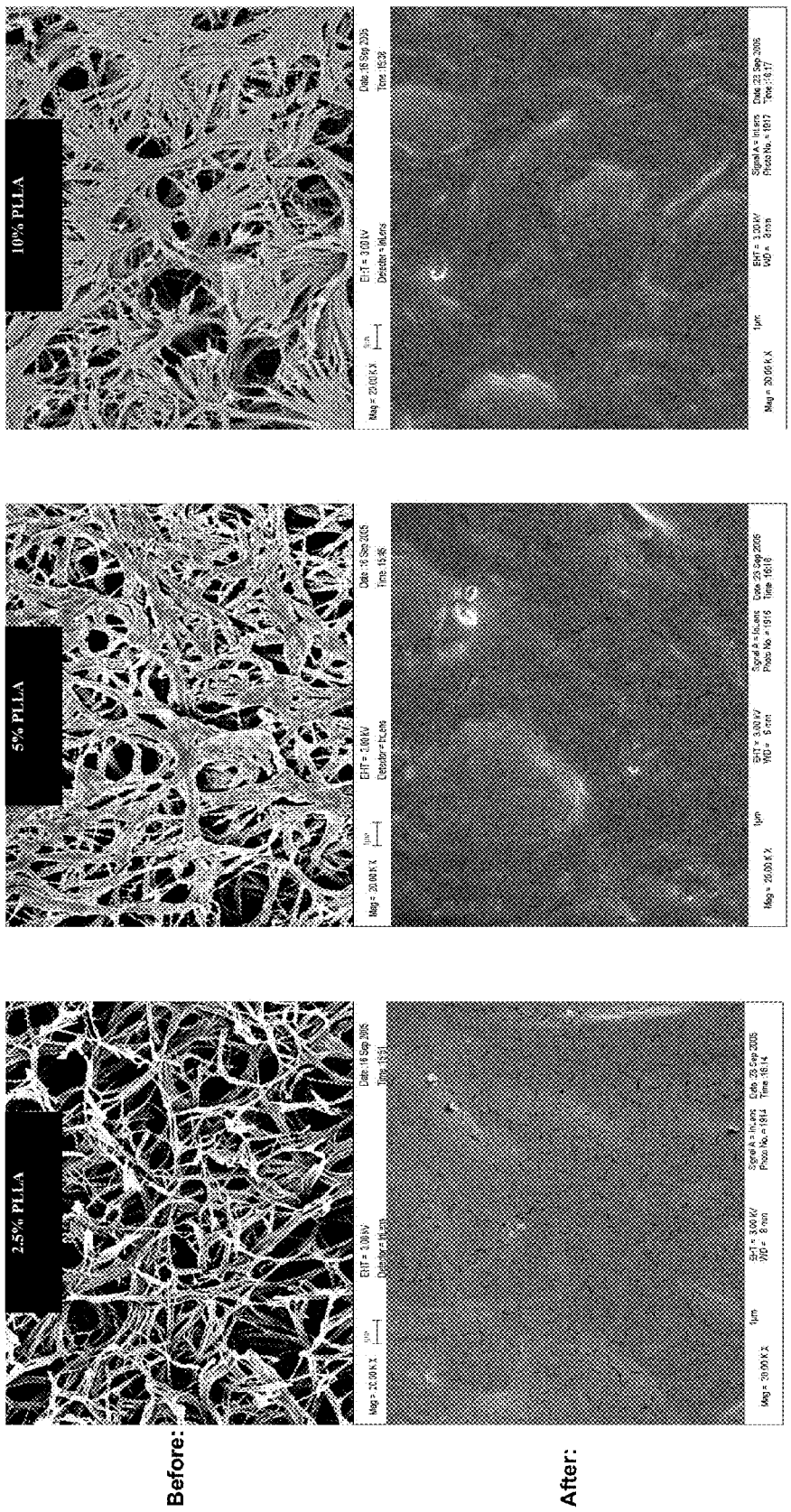
FIG. 3: SEM micrographs of PLLA nanoscaffolds before and after penetrating the pores with PDC. (Scale bars=1 μm).
Figure 7A:
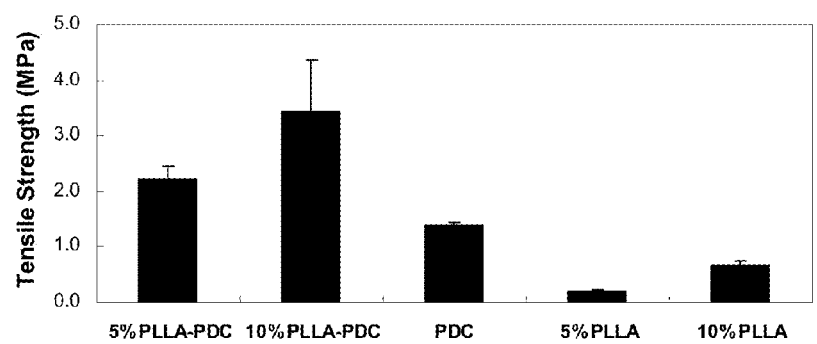
FIG. 7A-D—(A) Tensile strength, (B) Young's modulus, (C) Elongation at break of PLLA-PDC nanocomposites and controls that were polymerized at 80° C. for 3 day without vacuum (n=4). (d) Representative stress-strain curves. PLLA controls were not shown for clarity. (*p<0.05 from PDC control, # p<0.05 from PLLA control, $ p<0.05 comparing 5% PLLA-PDC to 10% PLLA-PDC).
Figure 7B:
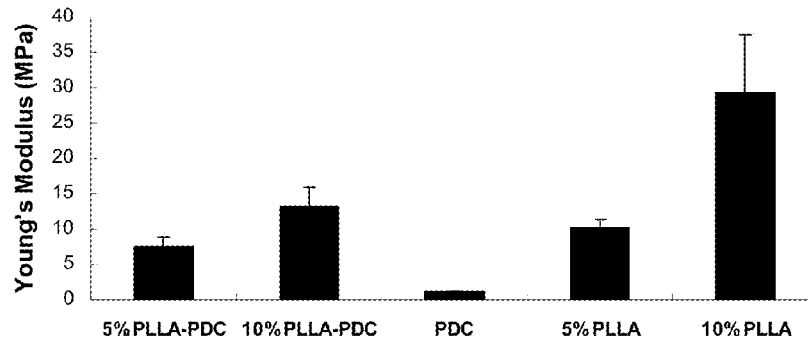
Figure 7C:
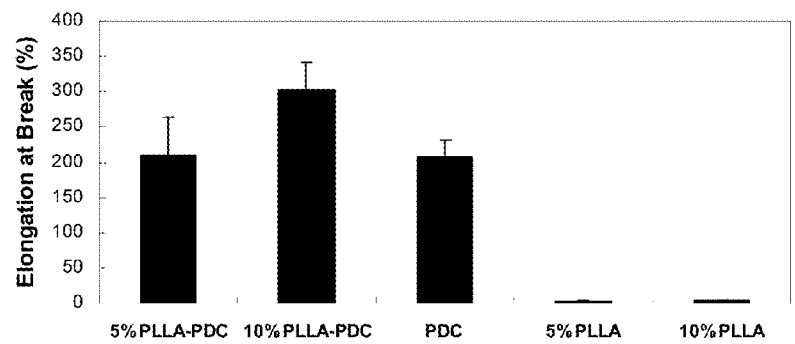
Figure 7D:
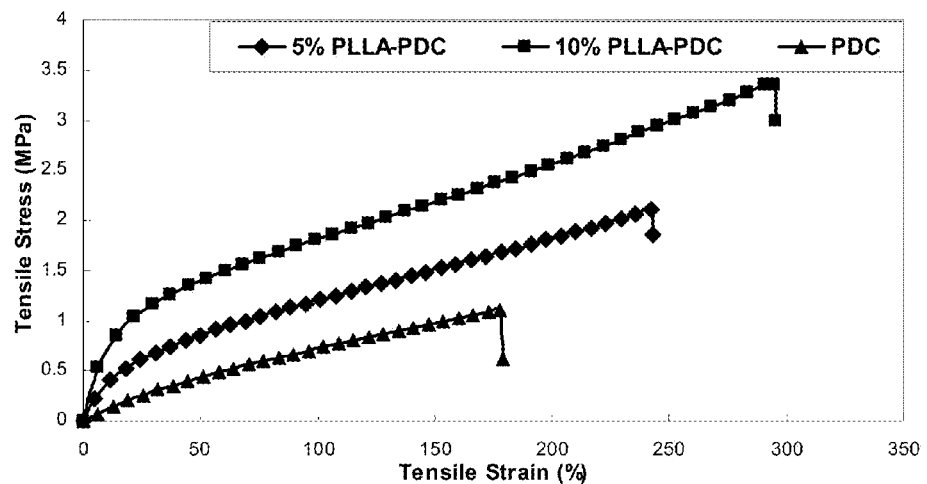

SEM micrographs of the PLLA nanoscaffolds and resulting composites are shown in FIG. 3) confirming that the nanopores were completely filled with PDC.

The mechanical properties of the composites are shown in FIG. 4). Increasing the PLLA concentration in the composite provides additional reinforcement and an increase in the tensile strength and modulus. The addition of the non-elastic PLLA nano-phase decreases the elongation at break. However, while the elongation at break decreased, the materials can still be elongated to many times there original length before breaking. A statistically significant difference was found when comparing the PDC control without PLLA and the PLLA-PDC nanocomposites, indicating that the mechanical properties can be increased using nanoscaffold composites.

Since both PLLA and PDC by themselves have been shown to be biocompatible, biodegradable, and capable of supporting cell adhesion and proliferation, it is believed that these composites will possess the same properties. Therefore it is anticipated that these materials will be applicable to tissue engineering.

Nanoparticle Results

Nanoparticles were produced using a spontaneous emulsion and solvent diffusion method [23, 25]. Both PLGA and PLLA nanoparticles were produced to allow the possibility of tailoring the degradation of the particles to that of the surrounding elastomeric matrix. As noted above the degradation can be adjusted by choice of lactic acid:glycolic acid ratio. The results of various nanoparticles produced in 1 gram batches using 2% polymer in solvent solutions are shown in Table (2) below.

TABLE (2)

Size and Polydispersity of various nanoparticles

| Sample | Size (nm) | Polydispersity | Recovery (%) |
|---|---|---|---|
| PLGA (85:15) | 178.1 | 0.005 | 103.84 |
| PLGA (50:50) | 190.1 | 0.005 | 99.23 |
| PLA | 177.4 | 0.005 | 98.00 |
| PLLA | 183.7 | 0.045 | 87.95 |

PLGA = poly(lactic-co-glycolic acid) with the ratio of lactic to glycolic acid designated by (Lactic:Glycolic)
PLA = poly(D,L-lactic acid)
PLLA = poly(L-lactic acid)

The modified spontaneous emulsion and solvent diffusion method was able to produce nanoparticles from PLGA of various ratios as well as poly(D,L-lactic acid) and poly(L-lactic acid). The low polydispersity for all nanoparticles indicates that the method produces uniform nanoparticles with little aggregation. A high recovery indicates that this method could potentially be scaled up to larger batches.

PLGA nanoparticles of various sizes were also produced by varying the concentration of polymer in solvent. Results are shown in Table (3) below. By varying the concentration of polymer in solvent, the size of the nanoparticles could be controlled. With rubber elastomers and carbon black, the increase in mechanical properties is inversely proportional to the size of the nanoparticles added [2]. Thus it is believed that the increase in strength and stiffness could be adjusted by changing the size of the nanoparticles.

TABLE (3)

Size of polydispersity of PLGA nanoparticles

| Concentration | Size (nm) | Polydispersity |
|---|---|---|
| 1% PLGA (85:15) | 166.8 | 0.033 |
| 2% PLGA (85:15) | 178.1 | 0.005 |
| 4% PLGA (85:15) | 216.9 | 0.051 |

For nanocomposite fabrication, 5 grams of PLGA (85:15) were made using a 2% PLGA solution. The diameter, poly(vinyl alcohol) content, and polydispersity of the nanoparticles used in the composite fabrication are shown in Table (4).

TABLE (4)

Nanoparticle Characteristics

| Diameter (nm) | 176.5 ± 6.8 |
|---|---|
| PVA Content (%) | 13.1 ± 2.6 |
| Polydispersity | 0.035 ± 0.038 |

Nanocomposites were fabricated with either 5% (w/w) or 10% (w/w) PLGA nanoparticles. SEM micrographs of the PLGA nanoparticles and resulting composites are shown in FIG. 5). FIG. 5A) shows the dried nanoparticles before incorporation into the PDC matrix. As can be seen, the nanoparticles are spherical and uniform in size. FIGS. (5B) and (5C) show the nanocomposite with nanoparticles embedded in the PDC matrix.

The mechanical properties of the composites are shown in FIG. 6). Nanoparticles added to the PDC matrix act as additional crosslink points and increase the strength and stiffness (Young's modulus) while decreasing the elongation at break. However, it should be noted that while the elongation at break decreases, the nanocomposites still maintain the ability to be elongated to many times their original length before rupture. A statistically significant difference was found when comparing the PDC control without nanoparticles to the PDC-PLGA nanocomposites, indicating that the strength and stiffness could be increased by incorporating nanoparticles.

Although in the present Example nanocomposites were created with poly(1,10-decanediol citrate), the methods of this Example may be applied to any elastomer or polymer that can be dissolved in common solvents. Thus, it is contemplated that the two methods used to produce nanocomposites could be applicable to other poly(diol citrates) or other elastomers such as poly(glycerol sebacate). Nanoscaffold or nanoparticle composites could be created with any polymer that can be dissolved in common organic solvents such as ethanol, acetone, 1,4-dioxane, etc. In addition, it has been demonstrated in other studies that the nanoprecipitation method can be used to encapsulate drugs and other small molecules [9-12]. This raises the possibility of creating drug releasing nanocomposites. Lastly, since PLGA and PDC by themselves have been shown to be biocompatible and biodegradable, these nanocomposites could readily be used for tissue engineering applications.

EXAMPLE 2

Biodegradable Poly(diol citrate) Nanocomposite Elastomers for Soft Tissue Engineering At present, synthetic biodegradable polymers commonly used for scaffolds in tissue engineering have a limited range of mechanical properties. This limitation is a challenge to in vivo tissue engineering, as the cell-scaffold construct is expected to maintain or restore normal tissue biomechanics during new tissue formation. The biodegradable elastomeric nanocomposite materials described in the present invention are such that their mechanical properties can be tailored to meet the requirements of soft tissue engineering applications. The nanocomposite consists of a nanofibrous poly(l-lactic acid) (PLLA) nanophase and an elastomeric poly(diol citrate) macrophase. Incorporation of a PLLA nanophase provides reinforcement to the poly(diol citrate) as demonstrated by an increase in tensile strength, modulus, and elongation at break with minimal permanent deformation. The mechanical properties of the nanocomposite were altered with the concentration of PLLA, choice of poly(diol citrate), and polymerization conditions. More importantly, the tensile mechanical properties compare favorably to that of human cartilage, ligament, and blood vessel. Furthermore, the compressive modulus is very similar to that of human and bovine articular cartilage. These results suggest that poly(diol citrate) nanocomposite elastomers are promising candidate biomaterials for soft tissue engineering.

Materials & Methods

The following materials and methods are similar to those already described in Example 1.

Poly(L-lactic acid) (Mw~50,000, polydispersity~1.8) was purchased from Polysciences (Warrington, Pa.). All other chemicals were purchased from Sigma-Aldrich (Milwaukee, Wis.).

Synthesis of poly(diol citrate) pre-polymer. Citric acid (50 g, 0.260 mol) and 1,8-octanediol (38.06 g, 0.260 mol) or 1,10-decanediol (45.36 g, 0.260 mol) were melted under a flow of nitrogen gas by stirring at 165° C. in a silicon oil bath and then stirred for another hour at 140° C. to create a pre-polymer solution of poly(1,8-octanediol-co-citrate) (POC) or poly(1,10-decanediol-co-citrate) (PDC). For nanocomposite preparation, the pre-polymer was dissolved in ethanol to a concentration of 30% (w/v).

Fabrication of Non-Porous Nanocomposites. The nanocomposite was fabricated in a two step process. Firstly, a PLLA nanofibrous network was fabricated via a thermally induced gelation followed by solvent exchange and freeze drying. [R. Zhang and P. X. Ma, J. Biomed. Mater. Res., 2000, 52, 430-438; P. Ma and R. Zhang, J. Biomed. Mater. Res., 1999, 46, 60-72] Secondly, the PLLA nanofibrous network was impregnated with the PDC or POC pre-polymer solution. Briefly, PLLA was dissolved in tetrahydrofuran (THF) to make solutions with concentrations of 5% and 10%. The PLLA solution was cast into a Teflon Petri dish to a thickness of approximately 1.5 mm and immediately placed into a −80° C. freezer for 1 hour to induce gelation. The gel was then transferred to a −20° C. freezer for 1 hour. After 1 hour, the dish containing the gel was removed from the −20° C. freezer and immersed in a large volume of ethanol for solvent exchange.

The ethanol was changed 3 times per day for two days to ensure complete removal of THF. Nanofibrous networks were transferred to a Teflon Petri dish and poly(diol citrate) pre-polymer in ethanol was poured over the nanofibrous network. The dish was subjected to repeated vacuum/repressurization cycles to ensure thorough penetration of the pre-polymer within the nanopores. Excess pre-polymer was removed from the dish and the nanocomposite polymerized at 60° C. for 4 hours. Following this step, the pre-polymer coating and vacuum/repressurization cycle was repeated once more. After the final coating, the composite was polymerized at 80° C. for 3 days without vacuum or 120° C. for 1 day without vacuum followed by 120° C. for 1 day with vacuum.

Fabrication of Porous Nanocomposite Scaffolds. Scaffolds were prepared using solvent casting and salt leaching techniques. Briefly, sodium chloride was ground using a mortar and pestle and sieved to obtain particles 90-120 µm in diameter. The salt particles were mixed with the PLLA in THF at a ratio of 10% PLLA and 90% salt by mass, packed into a Teflon Petri dish, and subsequently placed in a −80° C. freezer for 1 hour. The gel was then transferred to a −20° C. freezer for 1 hour. After 1 hour, the dish containing the gel was removed from the −20° C. freezer and immersed in a large volume of ethanol for solvent exchange. The composite was then coated with pre-polymer and polymerized as described above. After polymerization to crosslink the polymer, the Petri dish was soaked in a large volume of water to remove the salt. The water was changed twice a day for one week to ensure that the salt was removed. Complete removal of salt was checked by addition of silver nitrate to the water and observing for precipitation of silver chloride. The resulting scaffolds were freeze-dried in a Freezone 6 lyophilizer (Labconco, Kansas City, Mo.) and stored in a desiccator prior to use.

Characterization of Nanocomposites. Non-porous samples were tested for ultimate tensile strength, Young's modulus, and strain at break. Tensile tests were performed according to ASTM D412a on an Instron 5544 mechanical tester (Instron, Canton, Mass.) equipped with a 500N load cell. The size of the samples was (26 mm×4 mm×1.5 mm) and samples were pulled at a rate of 500 mm/min. From the stress-strain data, the ultimate tensile strength, Young's modulus, and elongation at break were calculated. Sample dimensions were measured before and after the tensile test to assess any permanent deformation.

To assess the potential use of the nanocomposites in cartilage tissue engineering, the compressive modulus of the salt-leached, porous scaffolds was evaluated in unconfined compression using a stepwise stress/relaxation test. [J. S. Jurvelin, M. D. Buschmann and E. B. Hunziker, P. I. Mech. Eng. [H], 2003, 217, 215-219; R. K. Korhonen, M. S. Laasanen, J. Töyräs, J. Rieppo, J. Hirvonen, H. J. Helminen and J. S. Jurvelin, J. Biomech., 2002, 35, 903-909] Briefly, scaffolds (~7 mm diameter, ~2 mm thickness) were loaded between two flat compression fixtures on an Instron 5544 mechanical tester and a series of fully automated stress relaxation steps (step 10 µm, velocity 1 µm/s) was repeated up to a 20% strain. A new step was automatically initiated after 2 minutes to ensure that equilibrium relaxation was reached. For each step, the complete time-position-load data were recorded. The compressive modulus was determined from the linear range (slope) of the stress-strain curve.

The porosity of scaffolds was measured using a method based on Archimedes' principle. [J. Yang, G. Shi, J. Bei, S. Wang, Y. Cao, Q. Shang, G. Yang and W. Wang, J. Biomed. Mater. Res., 2002, 62, 438-446] The morphology of nanofibrous networks and nanocomposites was studied using an LEO 1525 scanning electron microscope (Zeiss, Thornwood, N.Y.). SEM images were analyzed using image analysis software (Image-Pro® Plus V.5.0, Silver Spring, Md.) to obtain the pore size and fiber diameter data. Fifty measurements were averaged to get the mean value and standard deviation.

Data are expressed as means±standard deviation. The statistical significance between two sets of data was calculated using two-tail Student's t-test. Analysis of variance (ANOVA) and post-hoc analysis using the Tukey and Bonferoni tests were used to determine significant differences among three or more means. Data were taken to be significant, when a P-value of 0.05 or less was obtained.

Results & Discussion

POC and PDC composites were created using a PLLA nanofibrous network as a basis. It was hypothesized that a continuous nanofiber network would provide significant reinforcement to the resulting composite.

PLLA Nanofibrous Network Formation. Nanofibrous networks were produced through dissolution of PLLA in tetrahydrofuran (THF) followed by gelation at a preset temperature. Nanofibrous networks were created with PLLA concentrations of 5% or 10%. By varying the concentration of PLLA in THF, the characteristics of the nanofibrous network could be adjusted. Table (5) shows the characteristics of PLLA nanofibrous networks before the pores were filled with pre-polymer. All networks showed a wide distribution of nanometer scale pore sizes and fiber diameters with pore sizes ranging from 250-975 nm and fiber diameters from 100-300 nm. Increasing the PLLA concentration led to an increase in the network's density and fiber diameter while decreasing its porosity and pore size. A lower porosity decreases the amount of poly(diol citrate) macro-phase that would be incorporated into the final composite.

TABLE (5)

PLLA Nanofibrous Network Characteristics

|  | 2.5% PLLA | 5% PLLA | 10% PLLA |
| --- | --- | --- | --- |
| Fiber Diameter (nm) | 124.3 ± 27.3 | 246.3 ± 69.1 | 206.7 ± 70.4 |
| Density (g cm$^{-3}$) | 0.033 ± 0.007 | 0.063 ± 0.004 | 0.117 ± 0.006 |
| Porosity (%) | 97.37 ± 0.57 | 94.95 ± 0.32 | 90.56 ± 0.50 |
| Pore Size (nm) | 706.6 ± 266.1 | 643.8 ± 233.5 | 617.2 ± 362.9 |

Fabrication of poly(diol citrate)-PLLA nanocomposites. To create a nanocomposite, the nanopores within the PLLA network were filled with poly(diol citrate) pre-polymer and polymerized. SEM micrographs of the PLLA nanofibrous networks and resulting composites are shown in FIG. 2. The combination of PLLA nanofibrous networks and poly(diol citrate) elastomers resulted in a composite with increased mechanical properties. The mechanical properties and representative stress-strain curves of the composites with different percentages of PLLA are shown in FIG. 7). The presence of a PLLA nanofibrous network provided reinforcement to the poly(diol citrate) as demonstrated by the increased tensile strength, modulus, and elongation at break. Increases in tensile strength of 150% over the PDC control and 400% that of PLLA were seen with a 10% nanocomposite. Similarly, the modulus increased by 1000% compared to PDC without PLLA reinforcement. Although the modulus of the composite decreased relative to the PLLA network, the addition of the non-elastic PLLA nano-phase increased the elongation at break from 200% for the PDC control to 300% for the 10% nanocomposite. In contrast, the elongation at break for PLLA controls was less than 5%. PDC nanocomposites could be elongated to a much greater length with little permanent plastic deformation. The amount of permanent deformation after break of PDC scaffolds was less than 4% (Table 6). For the tensile strength, modulus, and elongation, a statistically significant difference was found when comparing the PDC control (no PLLA) and the PLLA-PDC nanocomposites, confirming that the mechanical properties could be significantly increased using nanofibrous composite elastomers.

TABLE (6)

Permanent Deformation

| Sample | Deformation (%) |
| --- | --- |
| 5% PLLA-PDC | 1.31 ± 0.14 |
| 10% PLLA-PDC | 3.27 ± 0.83 |
| 10% PLLA-POC | 1.88 ± 0.60 |
| PDC Control | 0.07 ± 0.30 |
| POC Control | 0.02 ± 0.20 |
| 5% PLLA Control | 0.10 ± 0.17 |
| 10% PLLA Control | 0.52 ± 0.52 |

The mechanical properties of the composites could be adjusted by varying the amount of PLLA in the final composite. Comparing between composites reinforced with different amounts of PLLA, there is an increase in the mechanical properties with increasing PLLA concentration from 5% to 10% (FIG. 7). The tensile strength, Young's modulus, and elongation at break increased by 54%, 75%, and 44%, respectively. The increase in mechanical properties with the addition of PLLA nanofibrous networks may be due to mechanical interlocking and/or interactions between the nanofibers and the elastomer chains.

With other nanofiber-reinforced composites, good nanofiber-matrix interaction is necessary to produce composites with increased mechanical properties. For this reason, researchers have attempted to functionalize the surface of the nanofibers within the composite to enhance bonding between the nanofiber and the surrounding matrix. [Finegan et al., *J. Mater. Sci.*, 2003, 38, 3485-3490; Blond et al., *Adv. Funct. Mater.*, 2006, 16, 1608-1614; Xu *J. Compos. Mater.*, 2004, 38, 1563-1582.] Within the compositions of the present invention, the high temperatures and release of water during the polycondensation of citric acid and a linear aliphatic diol likely partially hydrolyzes PLLA chains on the surface of the nanofibers yielding free carboxyl groups. These groups can then participate in ester bond formation with the poly(diol citrate) backbone, leading to covalent bond reinforcement. In addition, the use of nanofibrous networks instead of discontinuous fibers may help increase strength through mechanical interlocking between the PLLA nanofibers and the poly(diol citrate) chains.

Figure 8A:
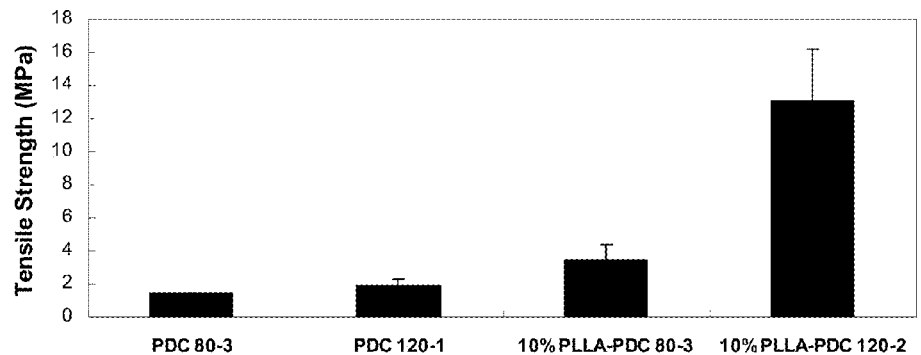
FIG. 8A-C—(A) Tensile strength, (B) Young's modulus, (C) Elongation at break of PLLA-PDC composites and controls that were polymerized at 80° C. for 3 day without vacuum or 120° C. for 1 day without vacuum then 120° C. for 1 day with vacuum (n=4). (*p<0.05 from PDC controls, # p<0.05 comparing between polymerization conditions for identical materials).
Figure 8B:
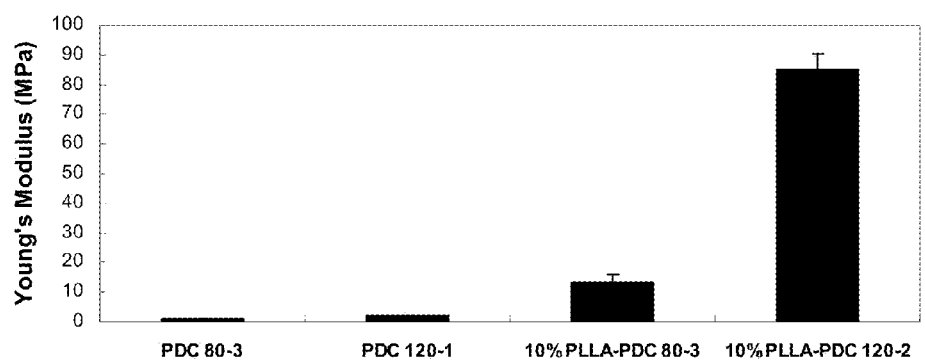
Figure 8C:
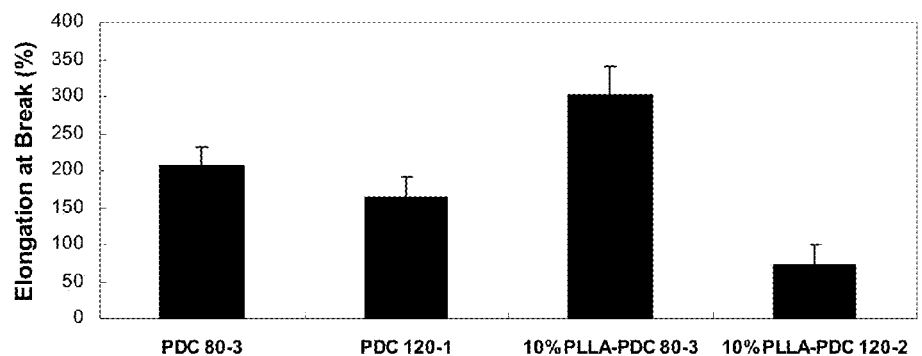

The effect of post-polymerization conditions on nanocomposite mechanical properties was also assessed. Increasing the polymerization temperature increased the tensile strength and modulus of the nanocomposite (FIG. 8). However, the elongation at break decreased significantly, although considerably larger than that of PLLA only. These results are not surprising as it has been previously reported that the strength and stiffness of poly(diol citrates) can be increased while decreasing the elongation at break through increased polymerization time and/or temperature. [Yang et al., *Biomaterials*, 2006, 27, 1889-1898; Yang et al., *Adv. Mater.*, 2004, 16, 511-516] These results suggest that it is possible to tailor the mechanical properties of the nanocomposite for specific soft tissue engineering applications such as cartilage, ligament, and blood vessel by changing polymerization conditions.

When compared to native tissue, the tensile mechanical properties of the highly polymerized 10% PLLA-PDC (tensile strength: 13.03±3.15 MPa, modulus: 85.13±5.52 MPa) compare favorably to that of cartilage and ligament (FIG. 8). For instance, the reported tensile strength of human cartilage and ligament are 3.7-10.5 MPa and 24-112 MPa, respectively. 2 Likewise, the reported Young's modulus of cartilage and ligament are 0.7-15.3 MPa and 65-541 MPa, respectively. Furthermore, the range of tensile strength values compares favorably to human coronary arteries (1.4-11.14 MPa). [He et al., *Tissue Eng.*, 2005, 11, 1574-1588] As noted above, mechanical properties are particularly important when engineering soft tissues which have specific biomechanical requirements for successful functional tissue engineering. [Lavik, E. and R. Langer, Tissue engineering: current state and perspectives. *Appl Microbiol Biotechnol*, 2004. 65: p. 1-8; Griffith, L. G., Polymeric Biomaterials. Acta Mater, 2000. 48: p. 263-277]

Figure 9A:
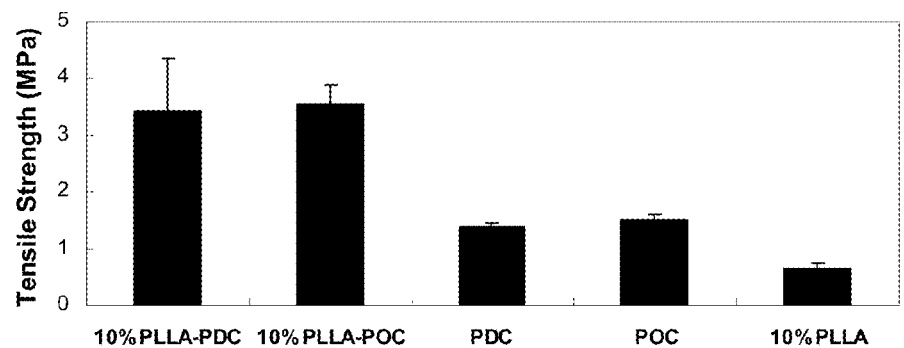
FIG. 9A-C—(A) Tensile strength, (B) Young's modulus, (C) Elongation at break of PLLA-PDC and PLLA-POC composites and controls that were polymerized at 80° C. for 3 day without vacuum (n=4) (*p<0.05 from poly(diol citrate) controls, # p<0.05 comparing between composite and PLLA control).
Figure 9B:
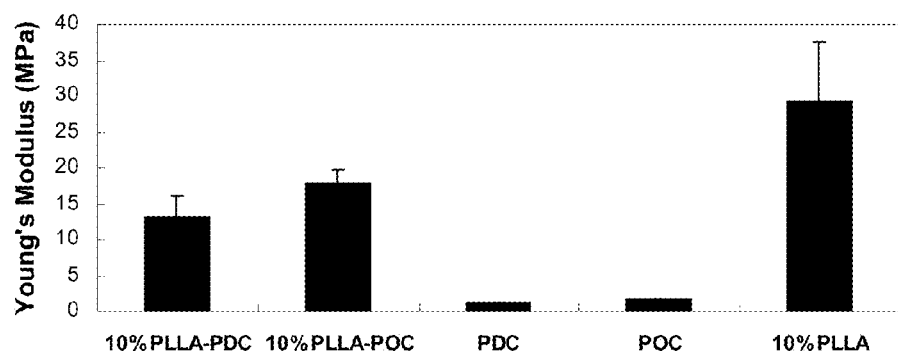
Figure 9C:
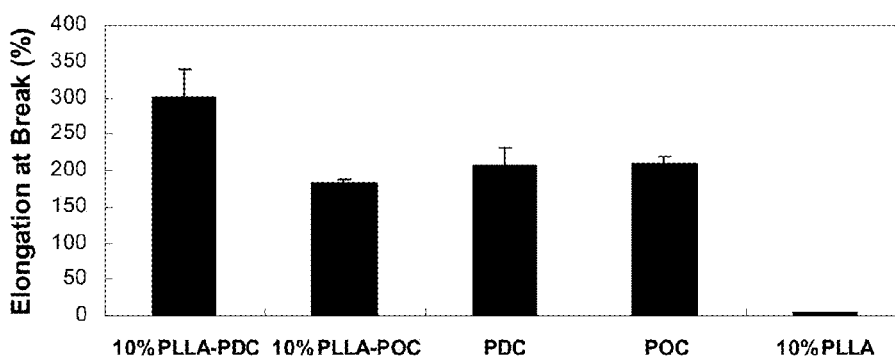

Although the mechanical properties of highly polymerized PDC-PLLA compare favorably to many soft tissues, it may be possible to further tailor the properties for specific applications through the selection of linear aliphatic diols of different carbon length. For this reason, nanocomposites of POC with PLLA were also fabricated. The mechanical properties of nanocomposites using POC and PDC with the same concentration of PLLA and identical polymerization conditions are shown in FIG. 9). For both materials, there is a statistically significant increase in the mechanical properties as compared to the poly(diol citrate) controls. Comparing between the composites, there is a statistically significant increase in Young's modulus when using the shorter chain 1,8-octanediol monomer relative to the longer 1,10-decanediol monomer. This finding is in agreement with published results for poly(diol citrates), as a shorter chain diol leads to a lower molecular weight between crosslinks and thus a greater crosslink density and increase in stiffness. [Yang et al., *Biomaterials*, 2006, 27, 1889-1898; Yang et al., *Adv. Mater.*, 2004, 16, 511-516] In addition, a longer chain diol can be elongated to a much greater length prior to break. [Yang et al., *Biomaterials*, 2006, 27, 1889-1898; Yang et al., *Adv. Mater.*, 2004, 16, 511-516]

Since poly(diol citrates) and PLLA by themselves have been shown to be biocompatible, biodegradable, and capable of supporting cell adhesion and proliferation, it was believed that these composites would possess similar properties.

Figure 10:
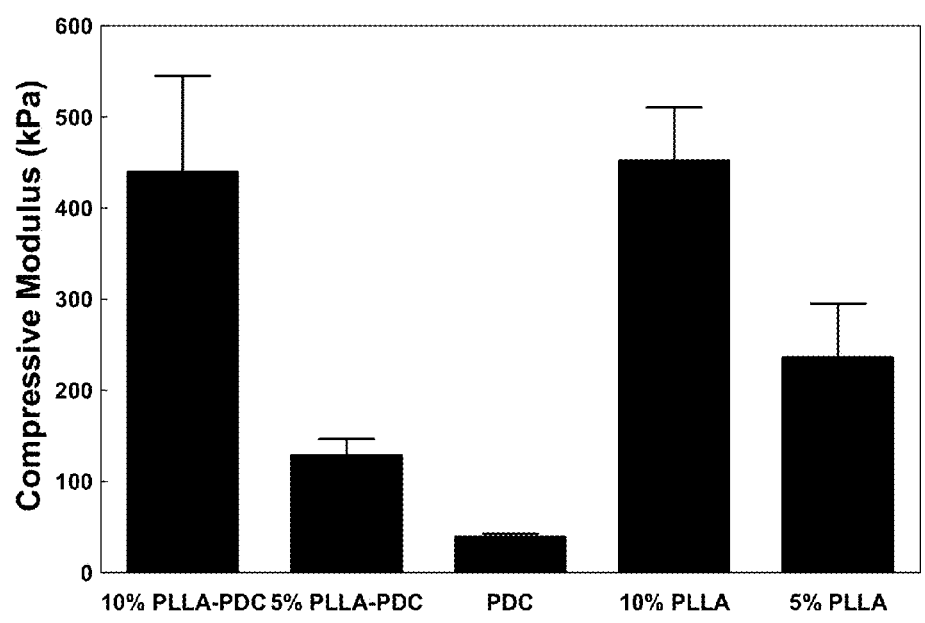
FIG. 10—Compressive modulus of PDC-PLLA nanofibrous scaffold composites. (*p<0.05 from PDC control, # p<0.05 from PLLA control, $ p<0.05 comparing between 5% PLLA-PDC and 10% PLLA-PDC)

Therefore it was contemplated that these materials could be used as scaffolds for tissue engineering. Porous nanocomposites were created through the incorporation of salt particles during the gelation step. [Zhang and P. X. Ma, *J. Biomed. Mater. Res.*, 2000, 52, 430-438] After gelation and solvent exchange with ethanol, the nanocomposite was created by impregnating the scaffold with poly(diol citrate) pre-polymer followed by polymerization and salt removal. The porosity of the nanofibrous scaffold composites is shown in Table (7). Both the 5% and 10% nanocomposites exhibited an open and interconnected pore structure with high porosity (FIG. 10). This feature is beneficial for tissue engineering applications as a three dimensional highly porous structure is required to support cell attachment, proliferation, and extracellular matrix synthesis. More importantly, the scaffold should possess mechanical properties that match the host tissue at the site of implantation. In relevance to cartilage tissue engineering, the mechanical properties of porous nanocomposites were tested in unconfined compression using a stepwise stress relaxation method commonly used with cartilage. [Jurvelin, *P. I. Mech. Eng. [H]*, 2003, 217, 215-219; Korhonen, *J. Biomech.*, 2002, 35, 903-909]. The compressive modulus increased with increasing PLLA concentration in the nanocomposite (FIG. 10). For the 10% PLLA-PDC concentration, the compressive modulus was 439±106 kPa, similar to that of human (581±168 kPa) and bovine (310±180 kPa) articular cartilage. [Jurvelin, *P. I. Mech. Eng. [H]*, 2003, 217, 215-219; Korhonen, *J. Biomech.*, 2002, 35, 903-909]. In addition, a statistically significant difference was found when comparing the PDC control scaffolds to the PLLA-PDC nanofibrous scaffolds.

TABLE (7)

Porosity of nanofibrous scaffold composites

| Sample | Porosity (%) |
|---|---|
| 10% PLLA-PDC | 83.14 ± 4.67 |
| 5% PLLA-PDC | 88.27 ± 4.47 |
| PDC Control | 92.50 ± 3.57 |

Although the degradation rate of PLLA may be too slow for most tissue engineering applications, it has been shown that nanofibrous PLLA scaffolds degrade at a significantly faster rate than solid walled counterparts. 37 While degradation was not examined in this study, it is believed that the degradation rate of the nanocomposite scaffolds would be increased compared to conventional PLLA microfiber or salt-leached scaffolds. The high nanofiber surface area in addition to the acidic degradation products of the poly(diol citrate) would contribute to faster observed degradation kinetics. In addition, the rate of degradation may be adjusted by varying the molecular weight of the PLLA used in composite fabrication.

In summary, in the present examples, novel nanocomposite elastomers were fabricated for potential use in soft tissue engineering using a poly(diol citrate) elastomeric macrophase and a nanofibrous network of poly(l-lactic acid). The incorporation of nanofibrous PLLA to the poly(diol citrate) increased tensile strength, Young's modulus, and elongation at break with little permanent deformation. In addition, it was demonstrated that the mechanical properties could be adjusted by varying the PLLA concentration in the nanophase, by choice of diol monomer used to synthesize the poly(diol citrate) elastomeric matrix, or by adjusting polymerization conditions. The range of mechanical properties spanned that of human cartilage, ligament, and blood vessel. This is the first report of a nanocomposite material for tissue engineering where the macro and nano phases are made from biodegradable and biocompatible synthetic co-polymers. These results warrant further study of poly(diol citrate) nanocomposite elastomers for soft tissue engineering and medical applications.

REFERENCES

The following references are referred to herein throughout using a numeric identifier. Each of these references is incorporated herein by reference in its entirety.

1. Yang, J., A. Webb, and G. Ameer, *Novel citric acid-based biodegradable elastomers for tissue engineering.* Advanced Materials, 2004. 16(6): p. 511-516.

2. Parkinson, D., *The reinforcement of rubber by carbon black.* British Journal of Applied Physics, 1951. 2: p. 273-280.

3. Bokobza, L. and O. Rapoport, *Reinforcement of natural rubber.* J. Appl. Polym. Sci., 2002. 85: p. 2301-2316.

4. Bokobza, L. and O. Rapoport, *Silica and Carbon Black Reinforcement of Natural Rubber.* Macromol. Symp., 2003. 194: p. 125-133.

5. Kim, H. W., H. E. Kim, and V. Salih, *Stimulation of osteoblast responses to biomimetic nanocomposites of gelatin-hydroxyapatite for tissue engineering scaffolds.* Biomaterials, 2005. 26(25): p. 5221-5230.

6. Ramay, H. R. and M. Zhang, *Biphasic calcium phosphate nanocomposite porous scaffold for load-bearing bone tissue engineering.* Biomaterials, 2004. 25(21): p. 5171-5180.

7. Liao, S. S., et al., *Hierarchically biomimetic bone scaffold material: nano-HA/collagen/PLA composite.* Journal of Biomedical Materials Research, 2004. 69(2): p. 158-165.

8. Zhang, S. M., et al., *Synthesis and biocompatibility of porous nano-hydroxyapatite/collagen/alginate composite.* Journal of Materials Science. Materials in Medicine, 2003. 14(7): p. 641-645.

9. Barichello, J. M., et al., *Encapsulation of Hydrophilic and Lipophilic Drugs in PLGA Nanoparticles by the Nanoprecipitation Method.* Drug Development and Industrial Pharmacy, 1999. 25(4): p. 471-476.

10. Bilati, U., E. Alleman, and E. Doelker, *Development of a nanoprecipitation method intended for the entrapment of hydrophilic drugs into nanoparticles.* European Journal of Pharmaceutical Sciences, 2005. 24: p. 67-75.

11. Boehm, A. L., et al., *Nanoprecipitation technique for the encapsulation of agrochemical active ingredients.* J. Microencapsulation, 2003. 20(4): p. 433-441.

12. Chorny, M., et al., *Lipophilic drug loaded nanospheres prepared by nanoprecipitation: effect of formulation variables on size, drug recovery, and release kinetics.* Journal of Controlled Release, 2002. 83: p. 389-400.

13. Ratner, B. D. and S. J. Bryant, *Biomaterials: where we have been and where we are going.* Annu Rev Biomed Eng, 2004. 6: p. 41-75.

14. Lavik, E. and R. Langer, *Tissue engineering: current state and perspectives.* Appl Microbiol Biotechnol, 2004. 65: p. 1-8.

15. Okada, M., *Chemical syntheses of biodegradable polymers.* Prog Polym Sci, 2002. 27: p. 87-133.

16. Griffith, L. G., *Polymeric Biomaterials.* Acta Mater, 2000. 48: p. 263-277.

17. Cadee, J. A., et al., *A comparative biocompatibility study of microsphere based on crosslinked dextran or poly(lactic-co-glycolic)acid after subcutaneous injection in rats.* J Biomed Mater Res, 2001. 56: p. 600-609.

18. Andreopoulos, A. G., M. Evangelatou, and P. A. Tarantili, *Properties of maxillofacial silicone elastomers reinforced with silica powder.* Journal of Biomaterials Applications, 1998. 13(1): p. 66-73.

19. Atala, A. and R. P. Lanza, *Methods of Tissue Engineering.* 2001, San Diego: Academic Press.

20. Webb, A., J. Yang, and G. A. Ameer, *Biodegradable Polyester Elastomers in Tissue Engineering.* Expert Opin. Bio. Ther., 2004. 4(6): p. 801-812.

21. Ma, P. and R. Zhang, *Synthetic nano-scale fibrous extracellular matrix.* J. Biomed Mater Res, 1999. 46: p. 60-72.

22. Murakami, H., et al., *Preparation of poly(DL-lactide-co-glycolide) nanoparticles by modified spontaneous emulsification solvent diffusion method.* International Journal of Pharmaceutics, 199. 187(143-152).

23. Murakami, H., et al., *Further application of a modified spontaneous emulsification solvent diffusion method to various types of PLGA and PLA polymers for preparation of nanoparticles.* Powder Technology, 2000. 107: p. 137-143.

24. Matsumoto, T., et al., *The fate of the inverted segment of small bowel used for the replacement of major veins.* Surgery, 1966. 60(3): p. 739-43.

25. Murakami, H., et al., *Preparation of poly(DL-lactide-co-glycolide) nanoparticles by modified spontaneous emulsifcation solvent diffusion method.* International Journal of Pharmaceutics, 1999. 187: p. 143-152.

26. Alleman, E., et al., *In vitro extended-release properties of drug-loaded poly(DL-lactic acid) nanoparticles produced by a salting out method.* Pharmaceutical Research, 1993. 10: p. 1732-1737.

27. David, L. R., et al. *Spring-Mediated Cranial Reshaping for Craniosynostosis.* Journal of Craniofacial Surgery, 2004. 15: p. 810-816.

We claim:

1. A method, comprising:
   (a) combining a poly(diol citrate) pre-polymer solution with a nanostructured poly(L-lactic acid) to form a mixture;
   (b) polymerizing the mixture to form a nanocomposite comprising polymerized poly(diol citrate) and nanostructured poly(L-lactic acid);
   (c) hydrolyzing the poly(L-lactic acid) during the polymerization step to form free carboxyl groups on the surface of the nanostructured poly(L-lactic acid); and
   (d) forming covalent bonds between the free carboxyl groups on the surface of the hydrolyzed poly(L-lactic acid) and the polymerized poly(diol citrate).

2. The method of claim 1 wherein said poly(diol citrate) comprises monomers of citric acid and a linear diol comprising between 2 and 20 carbons.

3. The method of claim 2, wherein said poly(diol citrate) comprises citric acid and 1,8-octanediol monomers.

4. The method of claim 2, wherein said poly(diol citrate) comprises citric acid and 1,10-decanediol monomers.

5. The method of claim 1, further comprising a step of removing solvent and/or water before the polymerizing step.

6. The method of claim 1 wherein said poly(diol citrate) comprises two different linear diol monomers.

7. The method of claim 1, wherein said nanostructured poly(L-lactic acid) is fabricated into nanofibers.

8. The method of claim 1, wherein said nanostructured poly(L-lactic acid) is formulated into nanoparticles.

9. The method of claim 1, further comprising forming mechanically interlocked chains between the polymerized poly(diol citrate) and nanostructured poly(L-lactic acid).

10. The method of claim 1, wherein the nanostructured poly(L-lactic acid) has nanopores and wherein the combining step further comprises impregnating the nanopores with the poly(diol citrate) pre-polymer solution.

11. The method of claim 10, wherein the nanopores are completely filled with the poly(diol citrate) pre-polymer solution.

12. The method of claim 1, wherein said poly(diol citrate) comprises two different linear diol monomers, and wherein the method further comprises controlling the Young's modulus of the formed nanocomposite by varying the ratio of the two different linear diol monomer.

13. A nanocomposite produced by the method of claim 1.

14. A substrate for use in tissue engineering comprising the nanocomposite of claim 13 formulated into a cell culture substrate.

15. The substrate of claim 14, wherein said substrate further comprises a surface modification.

16. A drug delivery device comprising a drug interspersed in the nanocomposite of claim 13.

* * * * *